(12) United States Patent
Murray et al.

(10) Patent No.: US 11,278,358 B2
(45) Date of Patent: Mar. 22, 2022

(54) ASSEMBLY FOR COUPLING A PATIENT REFERENCE ARRAY TO A MEDICAL IMPLANT SUCH AS A PEDICLE SCREW

(71) Applicant: Medos International Sarl, Le Locle (CH)

(72) Inventors: James Murray, Quincy, MA (US); Marc Puls, Thörigen (CH); Daniel Thommen, Liestal (CH); Jörn Richter, Kandern (DE); Nicholas Pavento, North Attleboro, MA (US)

(73) Assignee: Medos International Sarl

( * ) Notice: Subject to any disclaimer, the term of this patent is extended or adjusted under 35 U.S.C. 154(b) by 368 days.

(21) Appl. No.: 16/412,033

(22) Filed: May 14, 2019

(65) Prior Publication Data

US 2020/0360091 A1    Nov. 19, 2020

(51) Int. Cl.
| | |
|---|---|
| A61B 17/58 | (2006.01) |
| A61B 17/60 | (2006.01) |
| A61F 2/00 | (2006.01) |
| A61B 34/20 | (2016.01) |
| A61B 17/70 | (2006.01) |

(52) U.S. Cl.
CPC .......... *A61B 34/20* (2016.02); *A61B 17/7076* (2013.01); *A61B 2034/2072* (2016.02)

(58) Field of Classification Search
CPC combination set(s) only.
See application file for complete search history.

(56) References Cited

U.S. PATENT DOCUMENTS

| | | |
|---|---|---|
| 6,856,828 B2 | 2/2005 | Cossette et al. |
| 7,753,910 B2 | 7/2010 | Ritland |
| 7,780,681 B2 | 8/2010 | Sarin et al. |

(Continued)

FOREIGN PATENT DOCUMENTS

| | | |
|---|---|---|
| EP | 3431032 A1 | 1/2019 |
| WO | 99/15097 A2 | 4/1999 |

(Continued)

OTHER PUBLICATIONS

Lambers et al., Morbidity and Safety of Iliac Crest Reference Array Pins in Navigated Total Hip Arthoplasty: A Prospective Cohort Study, The Journal of Arthoroplasty; 33 (2018) 1557-1561.

(Continued)

*Primary Examiner* — Sameh R Boles

(74) *Attorney, Agent, or Firm* — BakerHostetler

(57) ABSTRACT

In an embodiment, a system attaches a patient reference array of a computer-assisted surgery system to a patient. The system includes a fixation post having a shaft having proximal and distal ends that are offset from. A threaded fastener is coupled to the shaft at the distal end that rotates relative to the shaft so as to engage internal threads of a pedicle screw, thereby causing the distal end of the shaft to translate in the anchor seat and urge the pedicle screw to transition from an unlocked configuration to a locked configuration. The attachment assembly has an arm that supports the patient reference array, and a coupler supported by the arm.

(Continued)

The coupler has a fixation body that defines a recess that receives at least a portion of the fixation post, and an actuator that secures the attachment assembly to the fixation post.

8 Claims, 11 Drawing Sheets

(56) References Cited

U.S. PATENT DOCUMENTS

| | | |
|---|---|---|
| 8,317,844 B2 | 11/2012 | Maier et al. |
| 8,706,185 B2 | 4/2014 | Foley et al. |
| 9,005,211 B2 | 4/2015 | Brundobler |
| RE45,509 E | 5/2015 | Foley et al. |
| 9,585,700 B2 | 3/2017 | Wehrle et al. |
| 9,907,582 B1 | 3/2018 | Olea |
| 2008/0154262 A1 | 6/2008 | Brundobler |
| 2012/0232377 A1 | 9/2012 | Nottmeier |
| 2015/0257851 A1 | 9/2015 | Plassky et al. |
| 2017/0360515 A1 | 12/2017 | Kozak et al. |
| 2018/0092699 A1 | 4/2018 | Finley |
| 2018/0199951 A1 | 7/2018 | Chappuis et al. |
| 2018/0206860 A1 | 7/2018 | Van et al. |
| 2018/0214016 A1 | 8/2018 | Thommen et al. |
| 2018/0289426 A1 | 10/2018 | Dace |
| 2018/0368893 A1 | 12/2018 | Divincenzo et al. |
| 2019/0029736 A1* | 1/2019 | Wall .................. A61B 17/7091 |

FOREIGN PATENT DOCUMENTS

| | | |
|---|---|---|
| WO | 2017/221257 A1 | 12/2017 |
| WO | 2019/010203 A1 | 1/2019 |

OTHER PUBLICATIONS

Brainlab, Cleaning, Disinfection and Sterilization Guide, Revision 5.2, 2016, 180 pages.

Brainlab, HIP, Instrument User Guide, Revision 1.1, 2015, 110 pages.

DePuy Synthes, Navigation-Ready Instrument Catalog, Feb. 2016, 20 pages.

Mezger et al., Navigation in surgery, Langenbeck's Archives of Surgery, Apr. 1, 2013;398(4):501-514.

* cited by examiner

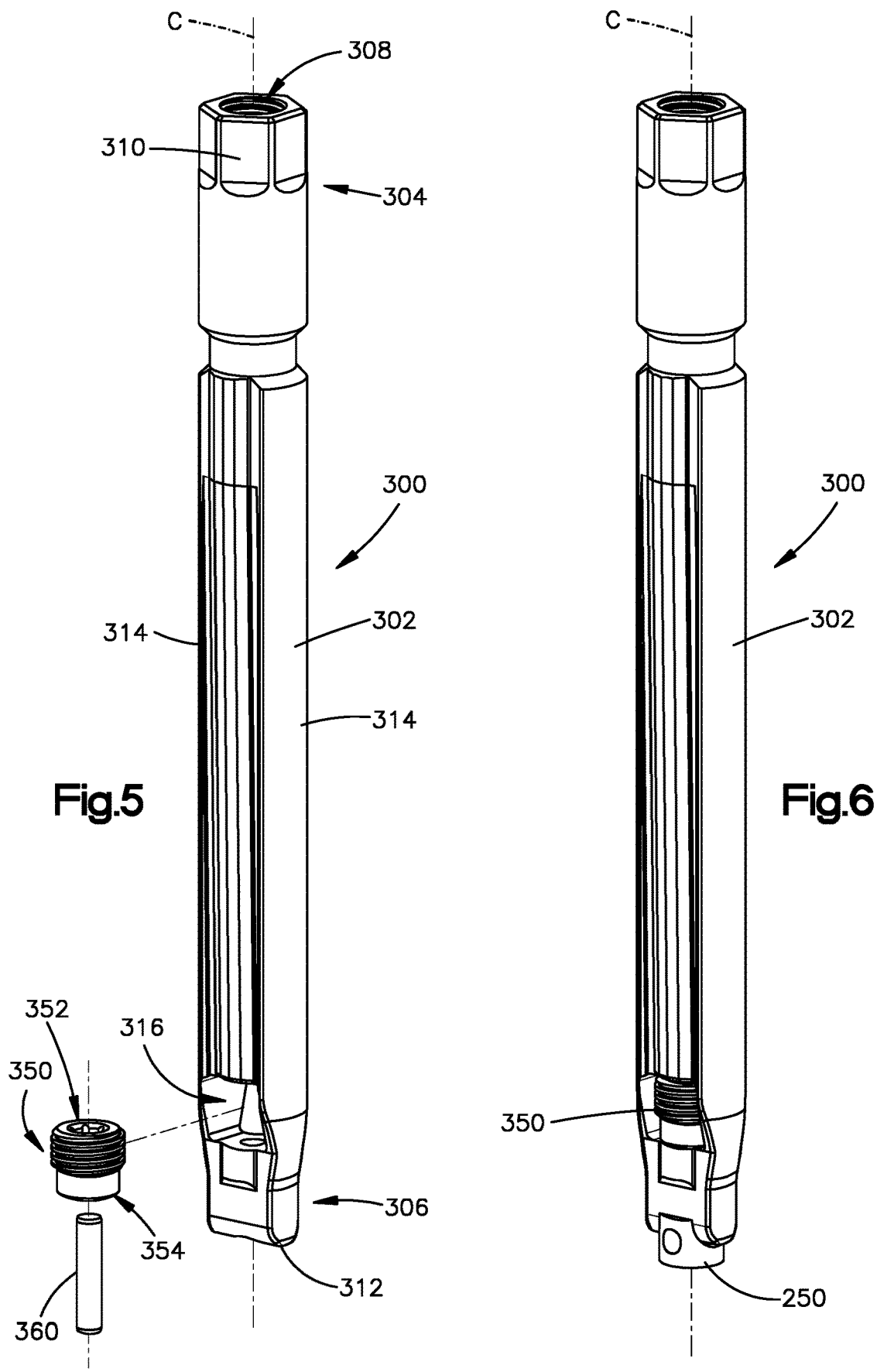

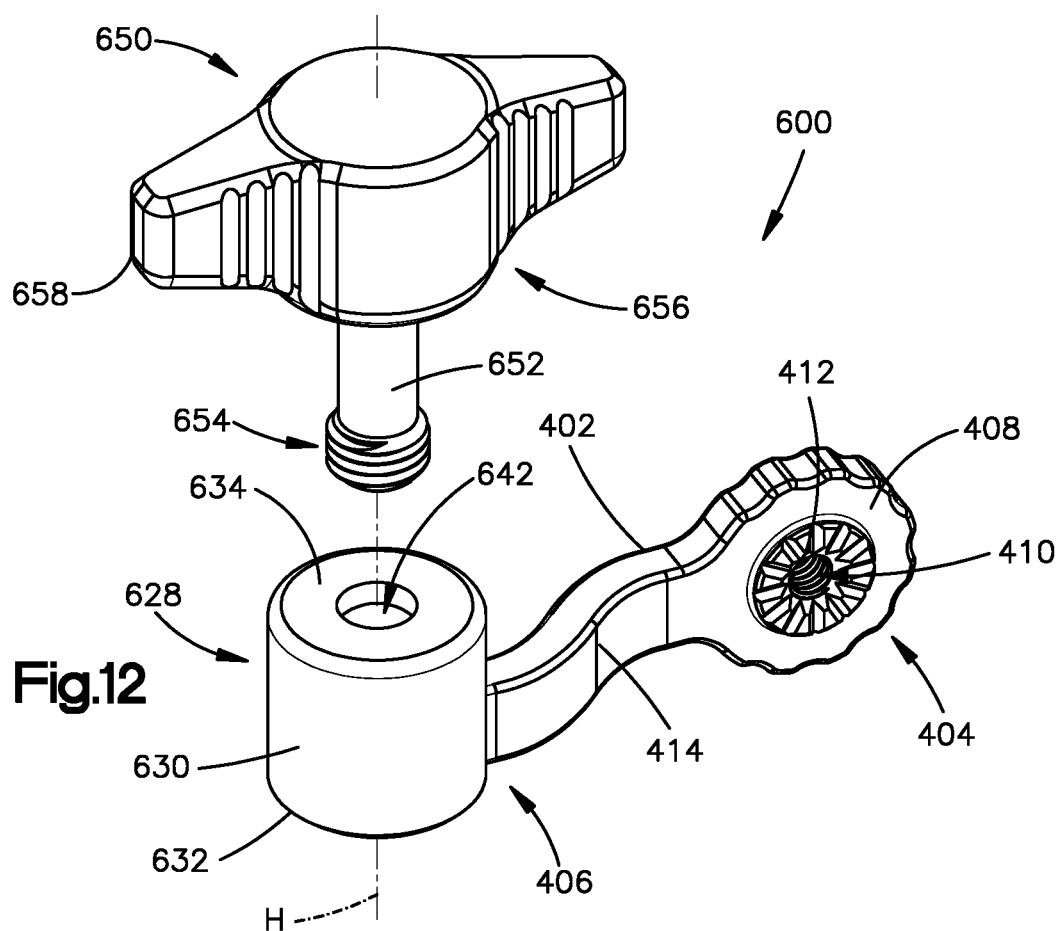
Fig.12
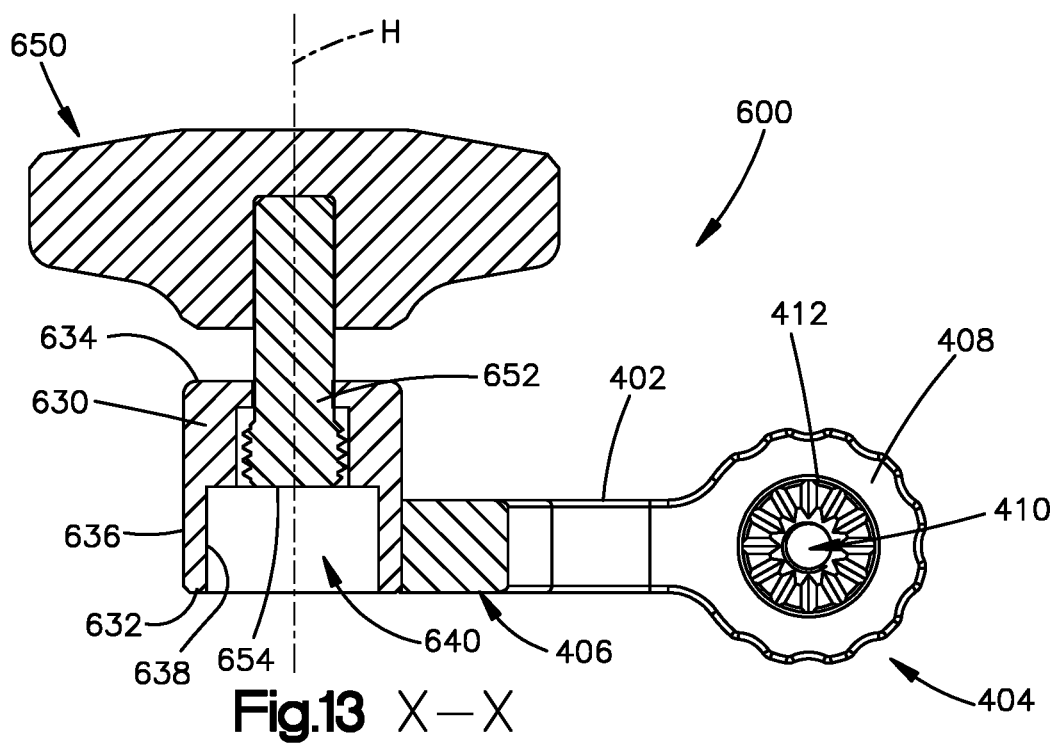
Fig.13 X—X

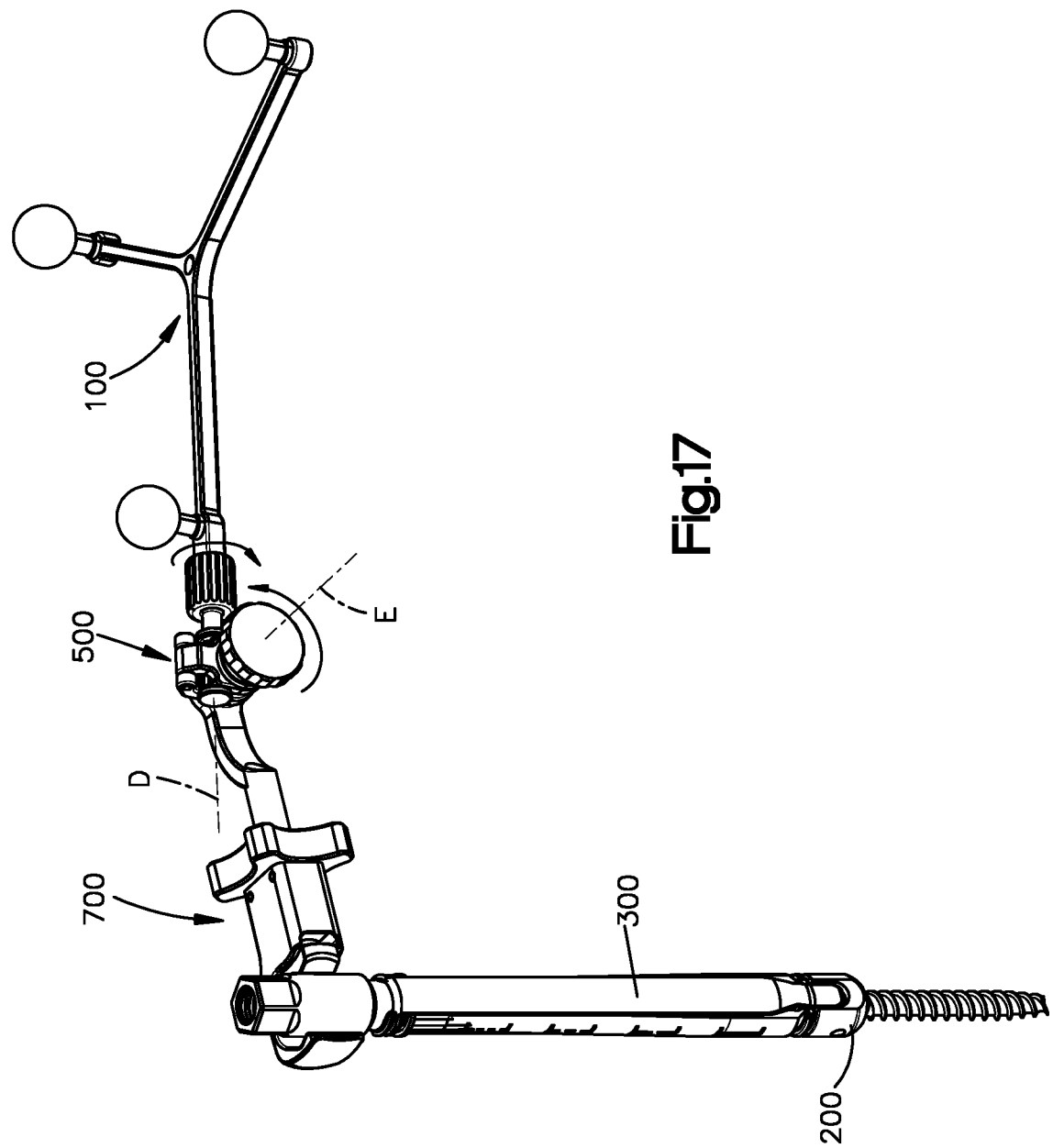

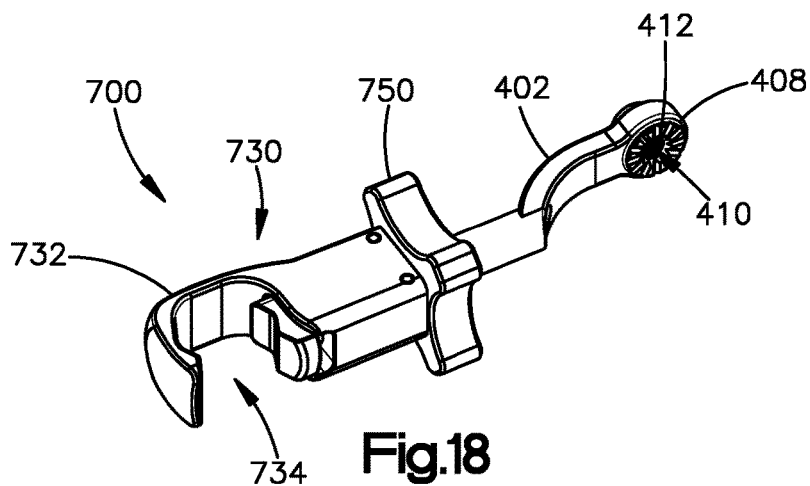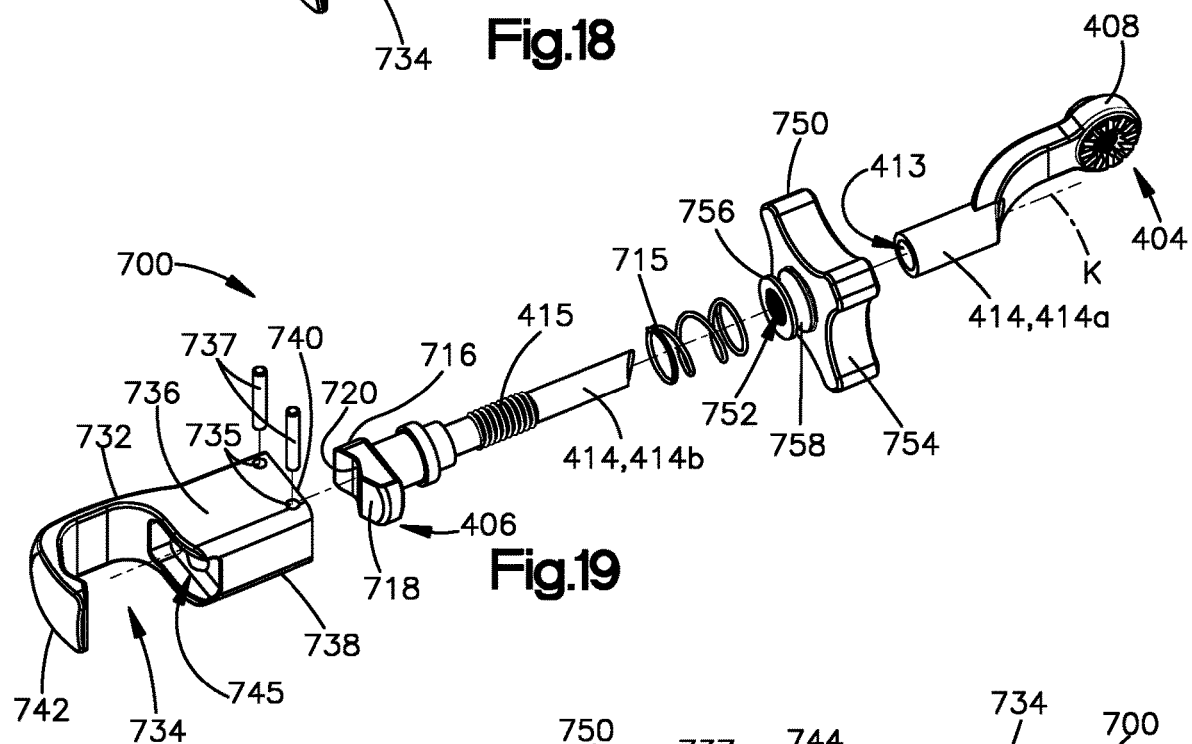

ASSEMBLY FOR COUPLING A PATIENT REFERENCE ARRAY TO A MEDICAL IMPLANT SUCH AS A PEDICLE SCREW

BACKGROUND

Computer-assisted surgery employs computer technology for surgical planning and for guiding surgical instruments during a surgery. Typically, in performing a computer-assisted surgery, a three-dimensional model of the patient is generated using medical imaging technologies such as one or more of MIII, CT scan, x-rays, and ultrasound. Sensors are positioned over the patient, and a computer system tracks movement of the surgical instruments relative to the three-dimensional model of the patient as the surgical instruments are sensed by the sensors. To aid in tracking movement of the surgical instruments, a patient reference array is typically attached to the patient prior to image collection that provides at least one reference point. Positioning of the instruments can then be tracked by the computer system relative to the at least one reference point. Surgeries performed using computer-assisted surgery techniques can typically reduce an amount of x-ray exposure to the patient compared to conventional non-computer assisted surgery techniques, and can often result in more accurate placement of medical implants.

SUMMARY

In accordance with one aspect of the present disclosure, a system is configured to attach a patient reference array of a computer-assisted surgery system to a patient. The system comprises a fixation post having a shaft that has a proximal end and a distal end that are offset from one another along a central axis. The fixation post has a threaded fastener at the distal end that is coupled to the shaft. The threaded fastener is configured rotate relative to the shaft about the central axis so as to engage threads of an anchor seat of a pedicle screw, thereby causing the distal end of the shaft to translate into the anchor seat along the central axis and urge the pedicle screw to transition from an unlocked configuration to a locked configuration. In the unlocked configuration, a screw of the pedicle screw is configured to pivot relative to the anchor seat of the pedicle screw. In the locked configuration, a position of the screw is fixed relative to the anchor seat of the pedicle screw. The system further comprises an attachment assembly that comprises an arm configured to support the patient reference array, and a coupler supported by the arm. The coupler comprises a fixation body defining a recess that is configured to receive at least a portion of the fixation post, and an actuator that is configured to secure the attachment assembly to the fixation post.

In accordance with another aspect of the disclosure, an attachment assembly is configured to attach a reference array of a computer-assisted surgery system to a medical implant. The attachment assembly comprises an arm configured to support the reference array, and a coupler. The coupler comprises a fixation body supported by the arm. The fixation body has a first end and a second end that are spaced from one another along a central axis. The fixation body has an inner surface that defines a recess that extends into the first end and terminates before the second end. The recess is configured to receive a proximal end of a shaft of the medical implant therein along the central axis. The attachment assembly further comprises an actuator coupled to the fixation body. The actuator has a shaft that extends into the recess and that is configured to be received in bore hole that extends into the proximal end of the shaft of the medical implant so as to secure the fixation body to the shaft of the medical implant.

In accordance with yet another aspect of the present disclosure, an attachment assembly is configured to attach a reference array of a computer-assisted surgery system to a medical implant. The attachment assembly comprises an arm configured to support the reference array, where at least a portion of the arm extends along a central axis. The attachment assembly comprises a coupler supported by the arm and configured to couple to the medical implant. The coupler comprises a fixation body movably coupled to the arm such that the fixation body is configured to translate along at least a portion of the arm along the central axis. The fixation body defines a recess that is configured to receive at least a portion of the medical implant. The coupler comprises an actuator that is coupled to the fixation body such that actuation of the actuator causes the fixation body to translate along the arm along the central axis so as to secure the fixation body to the medical implant.

BRIEF DESCRIPTION OF THE DRAWINGS

The following description of the illustrative embodiments may be better understood when read in conjunction with the appended drawings. It is understood that potential embodiments of the disclosed systems and methods are not limited to those depicted. In the figures:

FIG. 5 shows an exploded perspective view of the fixation post of FIG. 1 according to one embodiment;

FIG. 6 shows a perspective view of the fixation post of FIG. 1 engaging a collet of the pedicle screw of FIG. 1 according to one embodiment;

FIG. 12 shows an exploded perspective view of the attachment assembly of FIG. 11 according to one embodiment;

FIG. 13 shows a cross-sectional view of the attachment assembly of FIG. 11 according to one embodiment;

FIG. 17 shows a perspective view of a system of attaching a patient reference array to a pedicle screw according to yet another embodiment, the system including a fixation post and an attachment assembly that couples the patient reference array to the fixation post;

FIG. 18 shows a perspective view of the attachment assembly of FIG. 17 according to one embodiment;

FIG. 19 shows an exploded perspective view of the attachment assembly of FIG. 17 according to one embodiment; and FIG. 20 shows a cross-sectional view of the attachment assembly of FIG. 17 according to one embodiment.

DETAILED DESCRIPTION

Typically, when performing a computer-assisted spinal surgery, the patient reference array is either clamped onto a spinous process or attached to a dedicated pin or Schanz screw that is attached to the pelvic crest or a spinous process. The pin or Schanz screw is used only for supporting the reference array, and therefore, implantation of the pin or Schanz screw can require an additional incision to be made that might not otherwise be needed in a conventional, non-computer-assisted surgery. The additional incision can result in pain and irritation at the additional incision site. Further, the use of a dedicated pin or Schanz screw can leave holes in a bone, which could weaken the bone thereby preventing future attachment of implants should they be needed.

Instead of attaching the patient reference array to a dedicated pin or Schanz screw, the patient array can be attached to a medical implant, such as a pedicle screw assembly, that was either previously implanted during a prior spine fixation procedure or is being implanted for a current spine fixation procedure. Consequently, a separate incision need not be made to affix the patient reference array. The pedicle screw can be a monoaxial pedicle screw or a polyaxial pedicle screw. In the latter case, a position of the pedicle screw should be fixed so that the patient reference array does not move during the surgical procedure. Movement of the patient reference array can cause the computer-assisted surgical system to lose accuracy and/or calibration, thereby resulting in a time delay to recalibrate the system or errors in placement of medical implants. Therefore, embodiments of the present disclosure relate to systems that are configured to securely affix a patient reference array to a medical implant such as a pedicle screw so as to avoid movement of the patient reference array relative to the patient anatomy during a surgical procedure.

Figure 1:
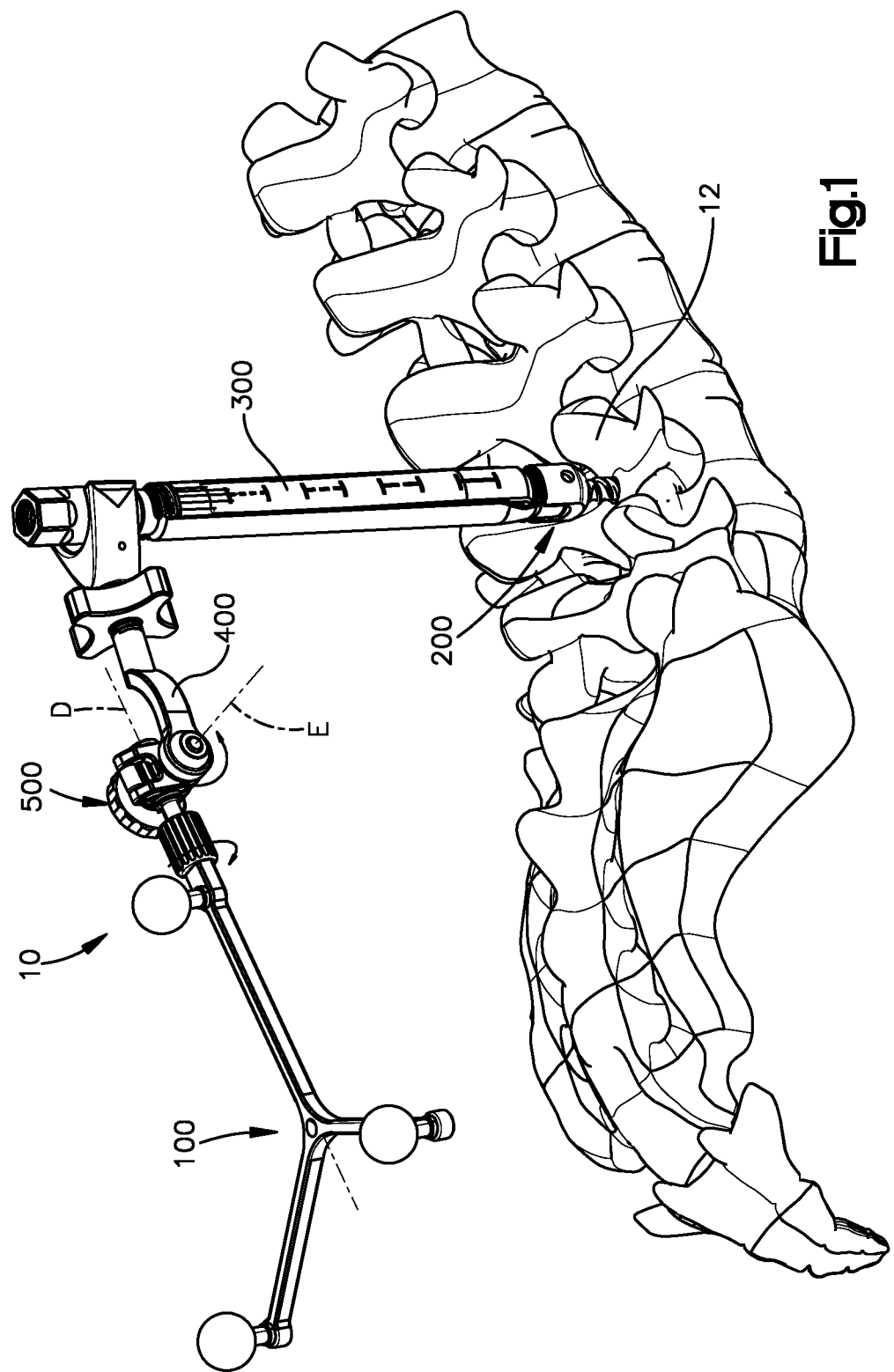
FIG. 1 shows a perspective view of a system of attaching a patient reference array to a pedicle screw that is implanted in a patient according to one embodiment, the system including a fixation post and an attachment assembly that couples the patient reference array to the fixation post.
Figure 11:
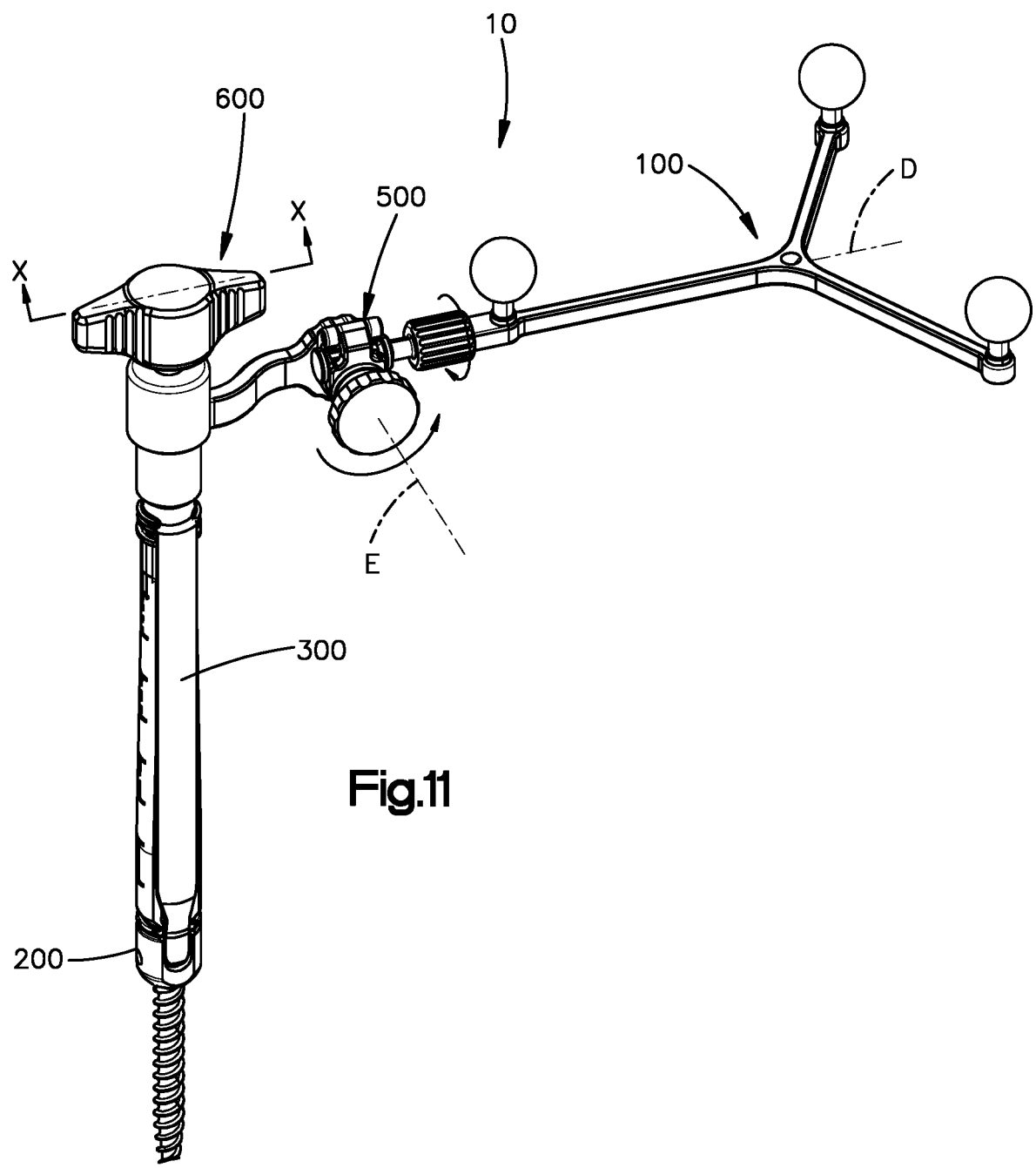
FIG. 11 shows a perspective view of a system of attaching a patient reference array to a pedicle screw according to another embodiment, the system including a fixation post and an attachment assembly that couples the patient reference array to the fixation post.

Referring to FIGS. 1, 11, and 17, according to various embodiments of the present disclosure, a system 10 is configured to attach a patient reference array 100 of a computer-assisted surgery system to a patient, such as a vertebra 12 of the patient. In general, the system 10 comprises at least one, such as both, of (i) a fixation post 300 that couples to a bone fixation element 200, such as a pedicle screw, and (ii) an attachment assembly (e.g., 400, 600, 700) that couples a patient reference array 100 to at least one of the bone fixation element 200 and the fixation post 300. The attachment assembly (e.g., 400, 600, 700) is configured to attach the patient reference array 100 to a medical implant, such as at least one of the bone fixation element 200 and the fixation post 300, so as to provide a rigid fixation between the attachment assembly and the medical implant. In some embodiments, the system 10 can further include at least one, such as both, of the patient reference array 100 and the bone fixation element 200.

Figure 2:
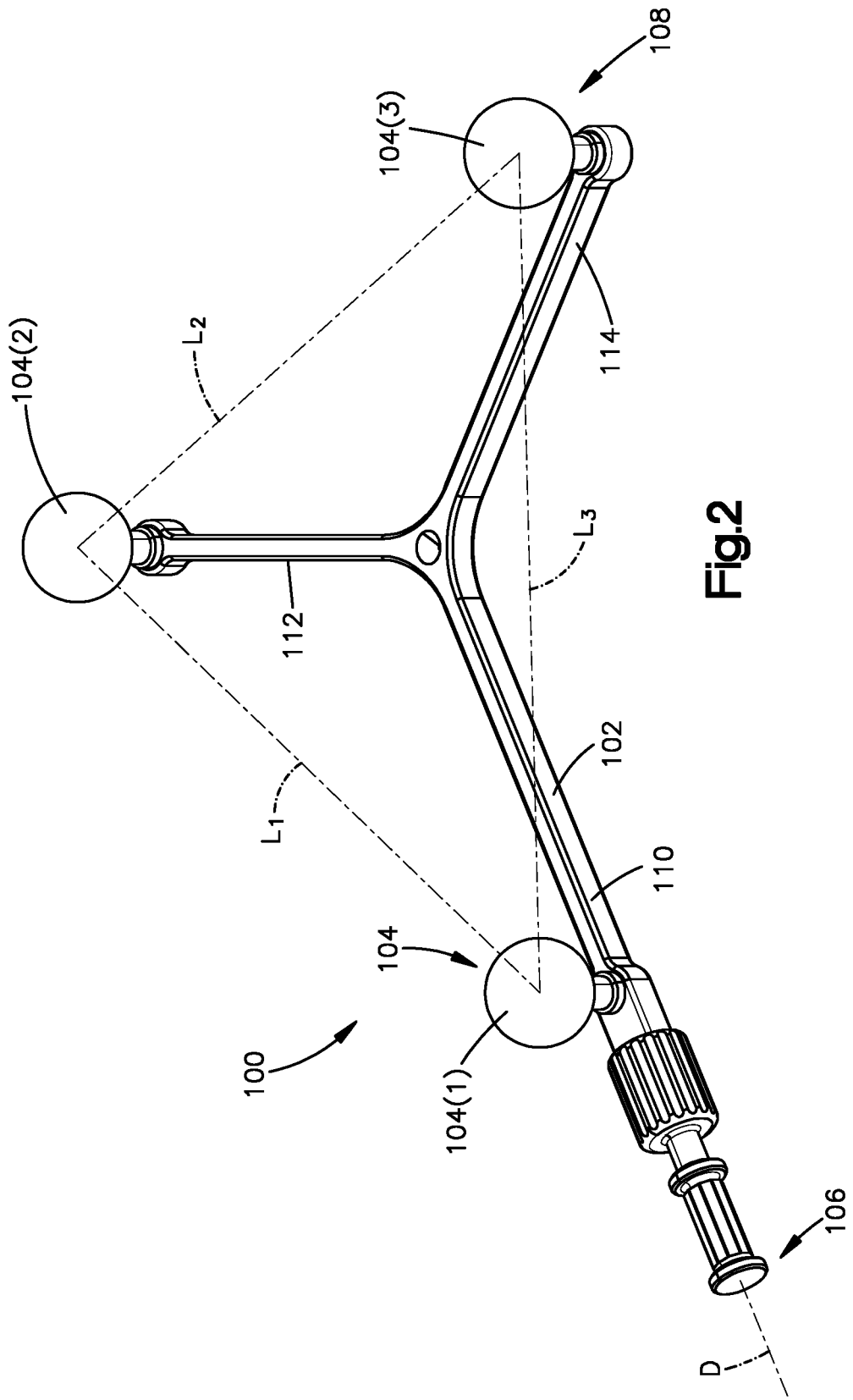
FIG. 2 shows a perspective view of a reference array body of the patient reference array of FIG. 1 according to one embodiment, the reference array body supporting a plurality of spherical markers.

Referring to FIG. 2, the patient reference array 100 can include a reference array body 102 that supports a plurality of markers 104. The markers 104 can be positionally fixed relative to the reference array body 102 when the markers 104 are coupled to the reference array body 102, such that movement of the reference body 102 causes corresponding movement of the markers 104. The plurality of markers 104 define at least one reference point that is detectable by a computer of the computer-assisted surgery system so that movement of a surgical instrument can be navigated relative to the at least one reference point. The plurality of markers 104 can include at least two markers 104, such as at least three markers 104, or such as at least four markers 104. Each marker 104 can be a protrusion that can have any suitable shape. For example, each marker can have a spherical shape or a partially spherical shape. Each marker 104 can be a passive marker, such as a reflective marker, that can be detected by at least one sensor or camera of the computer-assisted surgery system without actively communicating with the computer of the computer-assisted surgery system. Alternatively, each marker can be an active marker that is configured to actively communicate with the computing device of the computer-assisted surgery system.

The reference array body 102 can include a first end 106 and a second end 108 that are offset from one another. The first end 106 can be configured to removably couple to the attachment assembly (e.g., 400, 600, 700). For example, the first end 106 can define a shaft that is configured to couple to the attachment assembly. In some embodiments, at least a portion of the first end 106 can have a non-circular cross-section that is configured to engage with a non-circular cross-section of an adapter 500 or the attachment assembly so as to prevent rotation of the reference array 100 relative to the attachment assembly. For example, the non-circular shape can be a hexagon, an octagon, or any other polygon or suitable shape. It will be understood, however, that the first end 106 can define other suitable shapes or can be fixedly attached to the attachment assembly, such as monolithic with, adhered to, welded to, or otherwise fixedly attached to the attachment assembly.

The reference array body 102 can support the plurality of markers 104 such that the plurality of markers 104 are aligned in a common plane. In one embodiment, as shown, the markers 104 can be supported so as to define a triangle that connects the geometric centers of the markers 104. For example, the reference array body 102 can have a Y-shape or T-shape. The Y- or T-shaped body 102 can have a first shaft 110 that extends from the first end 106 towards the second end 108 along a central axis D. The first shaft 110 can support a first marker 104(1) of the plurality of markers 104. The first marker 104(1) can be supported adjacent the first end 106. The reference array body 102 can have a second shaft 112 and a third shaft 114 that extend from opposed sides of the first shaft 110. The second and third shafts 112 and 114 can support second and third markers 104(2) and 104(3) of the plurality of markers 104, respectively. The second and third markers 104(2) and 104(3) can be supported at the second end 108. The first and second markers 104(1) and 104(2) can be aligned along a first line L1. The second and third markers 104(2) and 104(3) can be aligned along a second line L2. The first and third markers 104(1) and 104(3) can be aligned along a third line L3. At least one, up to all, of the first, second, and third lines can be angularly offset from one another. For example, the first and second lines L1 and L2 can define an angle therebetween that is less than or equal to 90 degrees. The second and third lines L2 and L3 can define an angle therebetween that is less than or equal to 90 degrees. The first and third lines L1 and L3 can define an angle therebetween that is less than or equal to 90 degrees. It will be understood that, in alternative embodiments, the reference array body 102 can have other suitable shapes and/or the markers 104 can be supported so as to define other suitable shapes.

Figure 3:
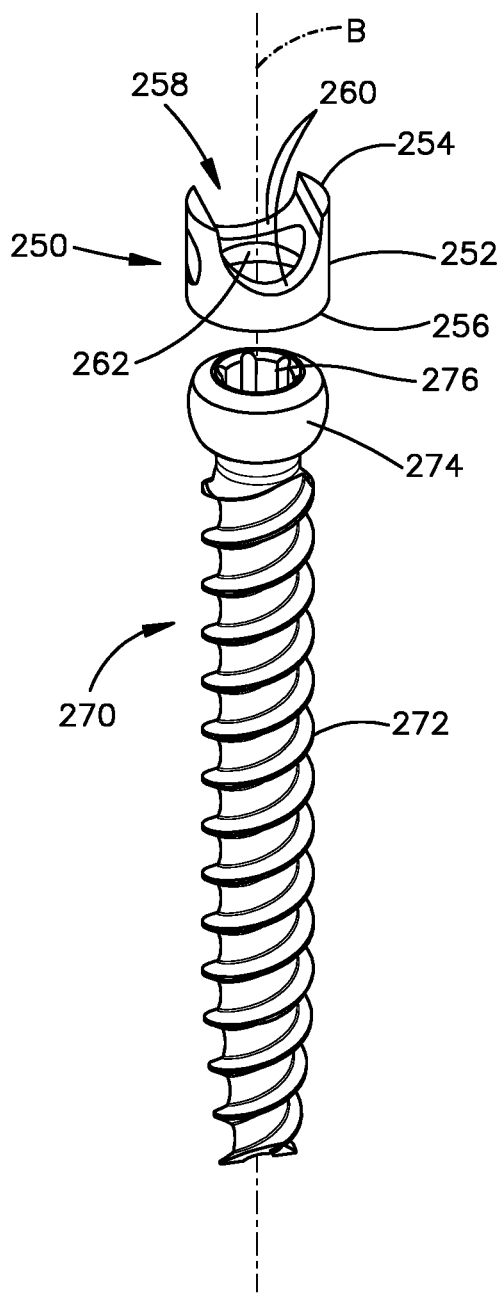
FIG. 3 shows an exploded perspective view of a bone anchor and collet of the pedicle screw of FIG. 1 according to one embodiment.
Figure 4:
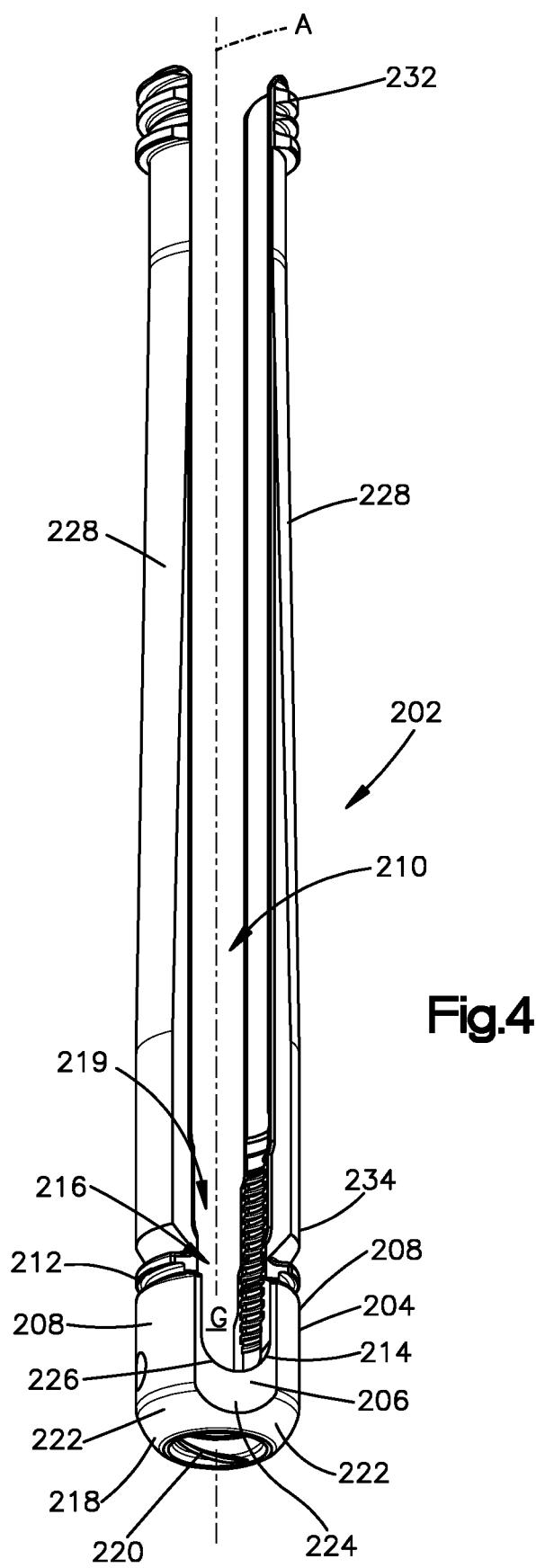
FIG. 4 shows a perspective view of an anchor seat of the pedicle screw of FIG. 1 according to one embodiment.

Turning now to FIGS. 3 and 4, an example bone fixation element 200 is shown. It will be understood that other bone fixation elements 200 are contemplated within the scope of the present disclosure, and that the present disclosure is not limited to use with the bone fixation element 200 shown in FIGS. 3 and 4. The bone fixation element 200 can comprise a bone anchor seat 202, a collet 250 configured to be disposed inside the anchor seat 202, and a bone anchor 270. The bone anchor 270 can include a head 274, and a shank 272 that extends from the head 274 along a central axis B. The head 274 can be enlarged to have a dimension along a radial direction that extends radially from the central axis B that is greater than a dimension of the shank 272 along the radial direction. The head 274 can be configured to be received in the anchor seat 202. In some examples, the head 274 can have a spherical shape, a partially-spherical shape such as a semi-spherical shape, or can alternatively have any suitable shape as desired to facilitate rotation with respect to the collet 250 as is described in more detail below. The head 274 can include a drive surface 276 configured to receive a corresponding tip of a drive tool, such as a screw driver configured to rotate the bone anchor 270 into engagement with the vertebrae 12 or other underlying bone surface. The drive surface 276 can define a hexagon, a star drive pattern, a Phillips head pattern, a slot for a screw driver, threads configured to receive corresponding threads of a threaded drive post, or any suitable drive tool engaging structure as desired.

The shank 272 can be attached at its upper end to the head 274. In at least some embodiments, the bone anchor 270 can be configured as a bone screw. Thus, the shank 272 can include external threading along at least a portion, such as an entirety, of the shank 272. The shank can define any suitable diameter, length, and thread design so as to engage the underlying bone, such as a vertebra 12. Alternatively, the shank 272 can be unthreaded so as to define a pin or a nail if desired. Thus, one skilled in the art will appreciate that the bone anchor 270 is not limited to any particular type of shank 272. The bone anchor 270 may be cannulated such that a central bore extends through the bone anchor 270 along the central axis B, or the bone anchor 270 may be solid along the central axis B (i.e., un-cannulated). In cannulated embodiments, the bone anchor 270 can optionally be fenestrated such that openings extend radially outward from the central bore to urge fluid out of the bone anchor 270 during injection or draw fluid into the central bore from the radial sides of the bone anchor 270 during extraction of material adjacent the bone anchor 270 if desired.

Referring more specifically to FIG. 4, the anchor seat 202 includes an anchor seat body 204. The anchor seat body 204 can be a generally tubular body extending along a central axis A. The body 204 includes a base 206 and a pair of arms 208 that extend out (up in illustrated the orientation) from the base 206. The arms 208 are spaced opposite one another so as to define a rod-receiving channel 210 therebetween. The arms 208 can be a mirror image of one another or can be a substantial mirror image of one another. As illustrated, each arm 208 can have an arc shape with an axis of the arc passing through a plane of symmetry that bisects the anchor seat 202. Each arm 208 extends circumferentially about its axis less than 180°, such as between 60° and 150°, for instance approximately 90°.

Each arm 208 has a first or upper end 212 and a second or lower end 214 that are offset from one another. The first or upper ends 212 define an upper end of the body 204. The upper end of the body defines an upper opening 216. The upper opening 216 can be defined between the first or upper ends 212 of the arms 208. The second or lower ends 214 of the arms 208 are attached to the base 206. The base 206 defines a lower end 218 that also defines the lower end of the body 204. The lower end 218 defines a lower opening 220. The body 204 defines an axial bore 219 extending from the lower opening 220 to the upper opening 216. The axial bore 219 is configured to receive the head 274 of the bone anchor 270 such that the shank 272 of the bone anchor 270 extends out the lower opening 220.

The arms 208 each have opposed circumferentially outer ends. The body 204 defines a pair of opposing gaps G that are spaced opposite from one another. Each gap is disposed between circumferentially adjacent outer ends of the arms 208. The opposing gaps G are in alignment with the axial bore 219. The arms 208 can be disposed radially opposite each other such that the gaps G, in combination with the aligned portion of the axial bore 219, define the rod-receiving channel 210. The rod-receiving channel 210 is sized and configured to receive a spine fixation rod such that the spine fixation rod extends through the anchor seat 202. The spine fixation rod can thus extend through the opposing gaps G and the axial bore 219. The arms 208 define radially inner and outer surfaces. The inner surface of each arm 208 has internal threading thereon. The threading is configured to threadedly receive a locking cap (not shown).

The base 206 includes a pair of spaced opposing support walls 222 and a pair of spaced opposing spacer walls 224 connected between the support walls 222. The arms 208 extend up from respective support walls 222, such that the spacer walls 224 are disposed between the arms 208. Each of the spacer walls 224 defines an upper end 226 that can be shaped as desired. The upper end 226 of each spacer wall 224 can be curved in accordance with the illustrated embodiment, such that the upper end 226 and the circumferentially outer ends of the arms 208 are adjoined to generally define a U-shape from a horizontal view through the gaps G. Thus, the upper ends 226 define the lower end of the gaps G. The upper ends 226 can be shaped to conform generally with the outer surface of the spine fixation rod, such that the gaps G receive the spine fixation rod during use. In one embodiment, the upper ends 226 can be spaced slightly below the upper surface of the collet 250, such that the spine fixation rod engages the collet 250 during use. Thus, the spine rod can bias the collet 250 towards the lower end 218 of the anchor seat 202, thereby locking a position of the bone anchor 270 relative to the anchor seat 202.

In some embodiments, the bone anchor seat 202 can include a pair of extension tabs 228 that are opposite one another. The extension tabs 228 are spaced opposite one another so as to define an upper portion of the rod-receiving channel 210 therebetween. Thus, the rod-receiving channel 210 can have an upper portion defined between the extension tabs 228 and a lower portion defined between the arms 208, where the upper and lower portions are aligned with one another along a direction that is parallel to the central axis A. The extension tabs 228 can be a mirror image of one another or can be a substantial mirror image of one another. As illustrated, each extension tabs 228 can have an arc shape with an axis of the arc passing through a plane of symmetry that bisects the anchor seat 202. Each extension tab 228 extends circumferentially about its axis less than 180°, such as between 60° and 150°, for instance approximately 90°. Thus, each extension tab 228 can have a cross-sectional shape that is substantially identical to, or similar to, a corresponding one of the arms 208.

Each extension tab 228 has a first or upper end 232 and a second or lower end 234 that are offset from one another. Each extension tab 228 can be elongate from its upper end 232 to its lower end 234. The upper ends 232 can define an upper end of the anchor seat 202. The lower end 234 of each extension tab 228 can be attached to a respective one of the arms 208, such as to an upper end 212 of a respective one of the arms 208. Each extension tab 228 can be removably attached to a respective arm 208. For example, each extension tab 228 can be configured to break away from its respective arm 208. Thus, the anchor seat 202 can define a joint between each extension tab 228 and its corresponding arm 208 that is configured to facilitate separation of the extension tab 228 and arm 208. In one example, each arm 208 can define a thickness from its inner wall to its outer wall, each extension tab 228 can define a thickness from its inner wall to its outer wall, and each joint can define a thickness from its inner wall to its outer wall that is less than the thicknesses of its corresponding arm 208 and extension tab 228. The inner wall of each extension tab 228 can include internal threading at its lower end 234.

Referring back to FIG. 3, the collet 250 includes a collet body 252 that defines a first or upper end 254 and a lower end 256 opposite from one another. The upper end 254 is sized and configured to contact or support at least a portion of a spine fixation rod (not shown) when the spine fixation rod is received within a rod-receiving channel of the anchor seat 202. The second or lower end 256 is sized and configured to contact or otherwise engage, directly or indirectly, a portion of the bone anchor head 274. The collet body 252 defines an axial bore 258 extending from the upper end 254 to the lower end 256. Thus, the collet body 252 can have an annular cross-sectional shape. The axial bore 258 is aligned with an axial bore 219 of the anchor seat 202 when the collet 250 is disposed in the anchor seat 202.

The upper end 254 of the collet 250 can define radially opposing upwardly facing seat portions 260 having a curvature or semi-spherical shape corresponding to the outer surface of the spine fixation rod (not shown). Therefore, the seat portions 260 can be configured to receive or otherwise support at least a portion (e.g., a lower portion) of the spine fixation rod. However, it will be understood that the upper end 254 can have other suitable shapes. The lower end 256 of the collet 250 has an inner surface 262 that defines a shape that conforms to the shape of the anchor head 274. For example, the inner surface 262 can have a partially-spherical shape. Thus, the inner surface 262 is configured to receive or otherwise engage at least a portion of the head 274. In alternative embodiments, the collet 250 can have an expandable lower end that includes, for example, spring fingers, where the expandable lower end is configured expand so as to pop onto the anchor head 274.

As will be described in further detail below with regards to FIGS. 7 and 8, the bone fixation element 200 can be configured such that, when the anchor head 274 of the bone anchor 270 is disposed in the anchor seat 202, the anchor head 274 can be moved between an unlocked position and a locked position. In the unlocked position, the bone anchor 270 can be configured to rotate relative to the collet 250 and/or anchor seat 202 about the central axis B. Additionally, or alternatively, in the unlocked position, the bone anchor 270 can be configured to pivot relative to the collet 250 and/or anchor seat 202 about at least one axis that is perpendicular to the central axis B. In at least some embodiments, the bone anchor 270 can be polyaxially pivotable relative to the collet 250 and/or the anchor seat 202 such that the bone anchor 270 pivots about a plurality of axes that are perpendicular to the central axis B. In the locked position, the collet 250 can engage the anchor head 274 so as to lock a position of the bone anchor 270 relative to the anchor seat 202.

Turning to FIGS. 5 and 6, the fixation post 300 comprises a fixation shaft 302 having a proximal end 304 and a distal end 306 that are offset from one another. The fixation shaft 302 can be elongate from the proximal end 304 to the distal end 306 along a central axis C. The distal end 306 of the fixation shaft 302 is configured to be received in the anchor seat 202 of the bone fixation element 200. In particular, the distal end 306 can have a distal end surface 312 that is configured to be received in the rod-receiving channel 210 between the arms 208 of the anchor seat 202. The distal end 306 can also be configured to engage the collet 250. For example, the distal end 306 can be configured to be received in the upwardly facing seat portions 260 of the collet 250. Thus, the distal end surface 312 can be configured the engage the upwardly facing seat portions 260.

At least a portion of the fixation shaft 302 is sized to be received between the extension tabs 228 when the fixation shaft 302 is received in the anchor seat 202. For example, the fixation shaft 302 can have at least one outer surface 314, such as a pair of opposed outer surfaces 314, that are configured to face and/or engage inner surfaces of the extension tabs 228. The fixation shaft 302 can have a cross-sectional shape that is conforms to a cross-sectional shape of the anchor seat 202 such that, when the fixation shaft 302 is disposed in the anchor seat 202, the fixation shaft 302 does not rotate relative to the anchor seat 202. The fixation shaft 302 can have a length along the central axis C that is sized such that the proximal end 304 extends beyond the arms 208 of the bone fixation element 200 (and optionally beyond the extension tabs 228 of the bone fixation element 200 in the event that the bone fixation element 200 is implemented with the tabs 228) when the distal end 306 of the fixation shaft 302 is seated in the anchor seat 202.

The proximal end 304 of the fixation shaft 302 can have any suitable configuration. For example, the fixation shaft 302 can define an opening 308 that extends into the proximal end 304 towards the distal end 306. The opening 308 can be configured to engage a protrusion of the attachment assembly (e.g., 400, 600, 700). For example, the opening 308 can define internal threads at the proximal end 304 that are configured to engage external threads of the attachment assembly (e.g., 400, 600, 700) as will be discussed below. Additionally, or alternatively, the fixation shaft 302 can have an outer surface 310 at the proximal end 304 that has a non-circular cross-section. The non-circular cross-section can be configured to engage a non-circular cross-section of the attachment assembly (e.g., 400, 600, 700) so as to prevent relative rotation between the fixation shaft 302 and the attachment assembly (e.g., 400, 600, 700).

The fixation post 300 has a threaded fastener 350 adjacent the distal end 306 that is rotatably coupled to the fixation shaft 302. The threaded fastener 350 can have a generally cylindrical outer surface with external threading disposed thereon. The threaded fastener 350 can be configured to rotate relative to the fixation shaft 302 about the central axis C. In one embodiment, the fixation shaft 302 can include a drive surface 352 at its proximal end that is configured to receive a corresponding tip of a drive tool, such as a screw driver configured to rotate the threaded fastener 350. The drive surface 352 can define a hexagon, a star drive pattern, a Phillips head pattern, a slot for a screw driver, threads configured to receive corresponding threads of a threaded drive post, or any suitable drive tool engaging structure as desired. The opening 308 can extend from the proximal end 304 of the fixation shaft 302 to the threaded fastener 350 so as to allow a drive tool to extend into the fixation shaft 302 to engage the drive surface 352 of the threaded fastener.

The threaded fastener 350 can be coupled to the fixation shaft 302 by any suitable fastener. For example, the distal end 306 of the fixation shaft 302 can include an opening 316 that extends into an outer surface of the fixation shaft 302 along a transverse direction that is transverse to the central axis C. The threaded fastener 350 can be disposed in the opening 316. The threaded fastener 350 can extend beyond the outer surface of the fixation shaft 302 on both sides of the opening 316 such that the threads of the fastener 350 can engage the threads of the anchor seat 202. To secure the threaded fastener 350 to the fixation shaft 302, the threaded fastener 350 can define an aperture 354 that extends into a distal end of the threaded fastener 350 therein along the central axis C, and the fixation post 300 can include an axle 360 that is configured to extend from fixation shaft 302 into the aperture 354 of the threaded fastener 350 such that the threaded fastener 350 rotates about the axle 360. In alternative embodiments (not shown), the threaded fastener can be disposed about an outer surface of the fixation shaft 302, such that the fixation shaft 302 defines an axle about which the threaded fastener rotates.

Figure 7:
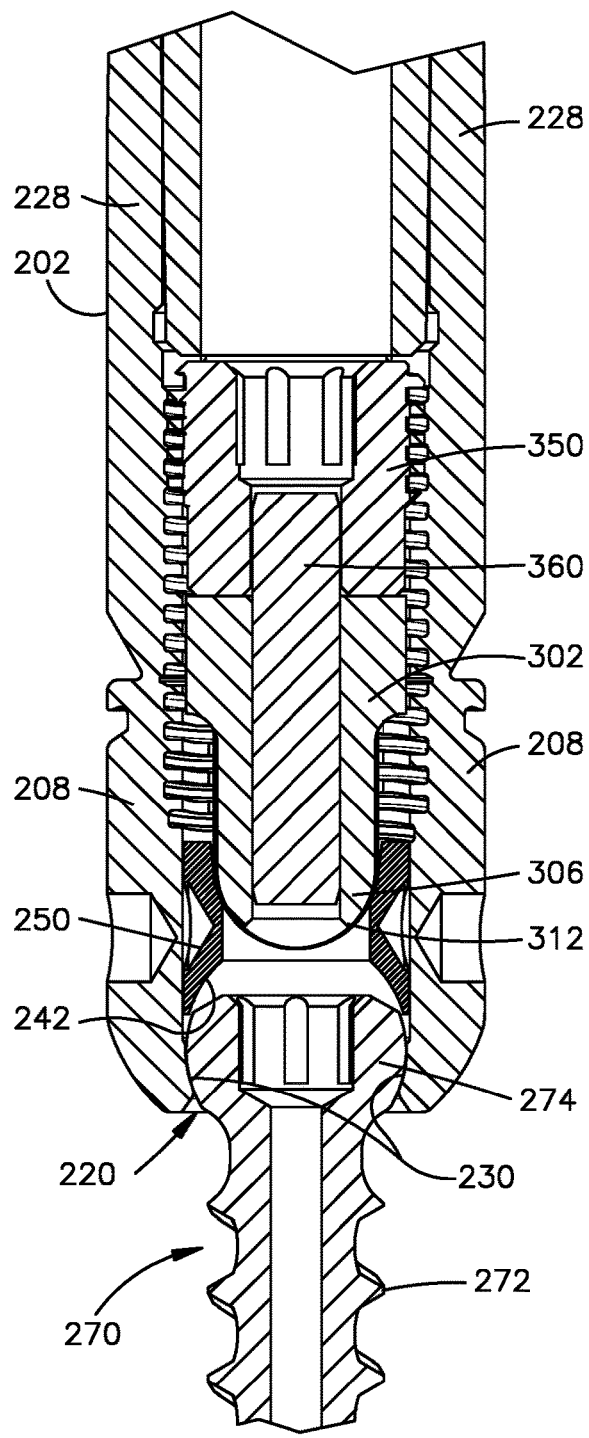
FIG. 7 shows a cross-sectional view of the fixation post and pedicle screw of FIG. 1 according to one embodiment, with the bone screw of the pedicle screw being in an unlocked position in which the bone screw is permitted to pivot.
Figure 8:
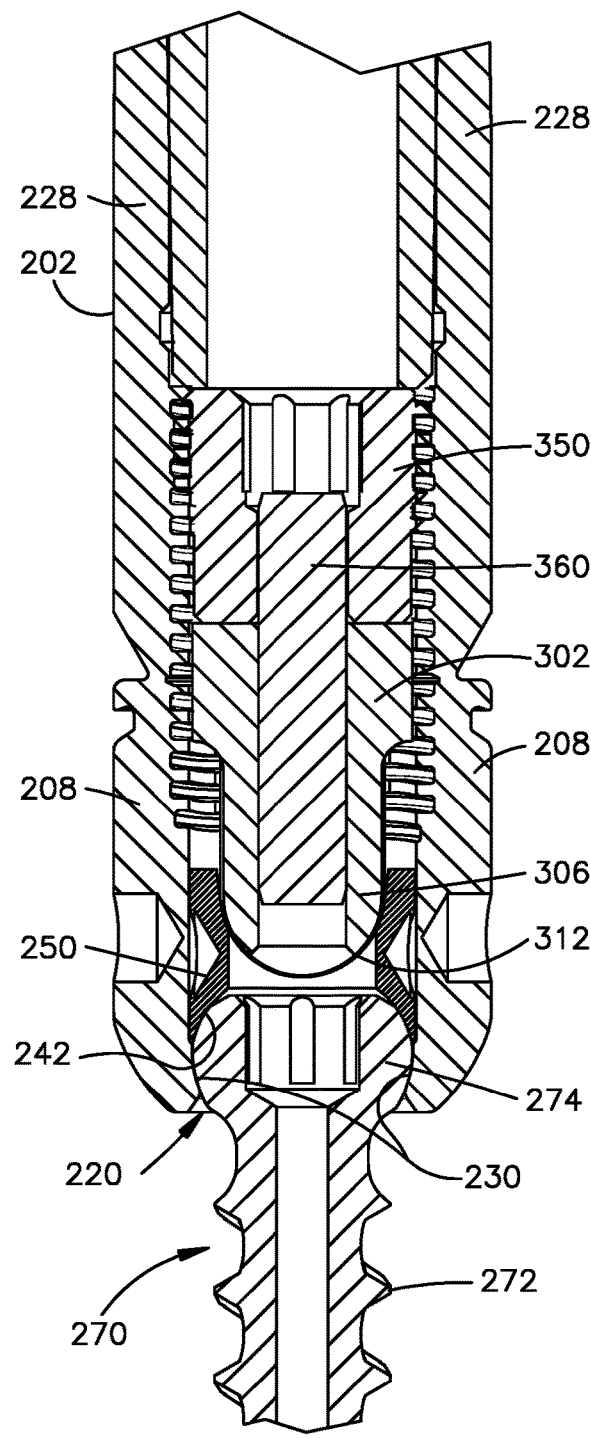
FIG. 8 shows a cross-sectional view of the fixation post and pedicle screw of FIG. 1 according to one embodiment, with the bone screw of the pedicle screw being in a locked position such that a position of the bone screw is fixed relative to an anchor seat of the pedicle screw.

Turning to FIGS. 7 and 8, the threaded fastener 350 is spaced from the distal end surface 312 of the fixation shaft 302 such that the threaded fastener 350 is configured to engage internal threading of the anchor seat 202, such as at least one of (i) the internal threads of the arms 208 of the anchor seat 202 and (ii) the internal threads of the extension tabs 228 of the anchor seat 202. Thus, the threaded fastener 350 is configured rotate relative to the fixation shaft 302 so as to engage the internal threads of the anchor seat 202, thereby causing the fixation shaft 302 to translate along the central axis C relative to the anchor seat 202. In particular, rotation of the threaded fastener 350 in a first rotational direction relative to both the fixation shaft 302 and anchor seat 202 can cause the distal end 306 of the fixation shaft 302 to translate into the anchor seat 202 along the central axis C. As the distal end 306 translates further into the anchor seat 202, the distal end 306 urges the bone fixation element 200 to transition from an unlocked configuration in FIG. 7 to a locked configuration in FIG. 8. In the unlocked configuration, the bone anchor 270 can be configured to rotate relative to the collet 250 and/or anchor seat 202 about the central axis B. Additionally, or alternatively, in the unlocked position, the bone anchor 270 can be configured to pivot relative to the collet 250 and/or anchor seat 202 about at least one axis that is perpendicular to the central axis B. In at least some embodiments, the bone anchor 270 can be polyaxially pivotable relative to the collet 250 and/or the anchor seat 202 such that the bone anchor 270 pivots about a plurality of axes that are perpendicular to the central axis B. In the locked position, a position of the bone anchor 270 is fixed relative to the anchor seat 202. In one example, in the locked position, the distal end 306 of the post 300 urges the collet 250 downward into the anchor seat 202. The collet 250 in turn urges the anchor head 274 downwards against an inner surface 230 of the anchor seat 202, thereby fixing a position of the anchor head 274 relative to the anchor seat 202.

Figure 9:
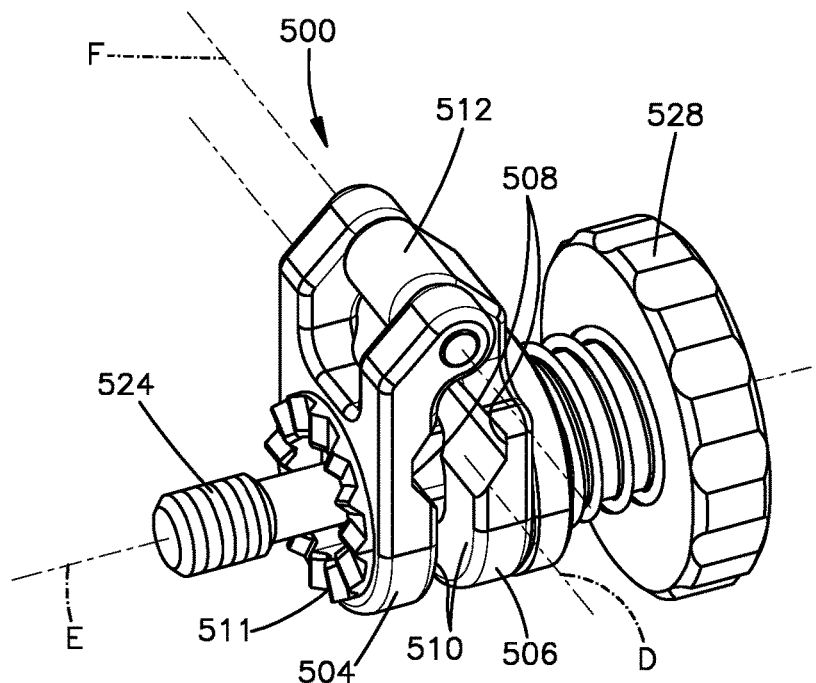
FIG. 9 shows a perspective view of an adapter of the patient reference array of FIG. 1 according to one embodiment, the adapter adapted to couple the reference array body of the patient reference array to the attachment assembly.
Figure 10:
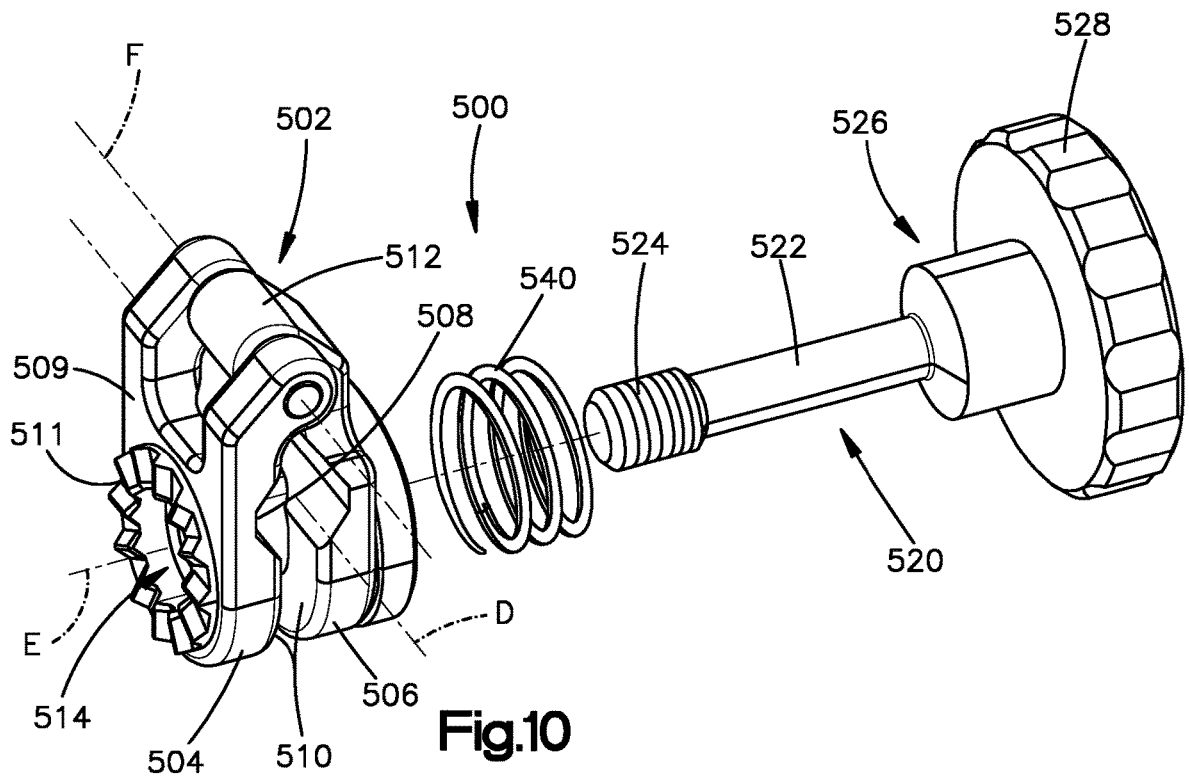
FIG. 10 shows an exploded perspective view of the adapter of FIG. 9 according to one embodiment.

Turning now to FIGS. 9 and 10, the attachment assembly (e.g., 400, 600, 700) can be configured to support the patient reference array 100. For example, the attachment assembly (e.g., 400, 600, 700) can be fixedly attached to the patient reference array 100, such as monolithic with, adhered to, welded to, or otherwise fixedly attached to the patient reference array 100. Alternatively, the attachment assembly (e.g., 400, 600, 700) can be removably couplable to the patient reference array 100. For example, as illustrated in FIGS. 1, 9, and 10, the system 10 can include an adapter 500 that is configured to removably couple the attachment assembly (e.g., 400, 600, 700) to the reference array body 102 of the patient reference array 100. The adapter 500 can be implemented as a StarLink adapter manufactured by Brainlab AG, or as any other suitable adapter that can couple the attachment assembly (e.g., 400, 600, 700) to reference array body 102.

The system 10 can include a joint that is configured to enable the reference array 100 to be selectively rotated about at least one axis so as to allow the patient reference array 100 to be repositioned relative to at least one sensor or camera of the computer-assisted surgery system. The joint can be implemented by the adapter 500 or another suitable component of the system 10. The joint can be configured to enable the reference array 10 to be selectively rotated about the central axis D of the patient reference array 100. Additionally, or alternatively, the adapter 500 can be configured to enable the reference array 10 to be selectively rotated about the central axis E that is perpendicular to the axis D of the reference array 100. The adapter 500 can be configured to lock a position of the reference array 100 after the reference array 100 has been selectively rotated.

With specific reference to FIGS. 9 and 10, the adapter 500 can include a clamp 502. The clamp 500 can be configured to move between an unclamped position and a clamped position when the first end 106 of the reference array body 102 is received therein. In the unclamped position, the clamp 500 can permit the reference array body 102 to (i) translate relative to the clamp 500 along a first direction that is parallel to the axis D of the patient array 100, and/or (ii) rotate relative to the clamp 500 about the axis D. In the clamped position, the clamp 500 positionally fixes the reference array body 102 relative to the clamp 502 with respect to at least one, such as both, of (i) translation along the first direction that is parallel to the axis D of the patient reference array 100, and (ii) rotation about the axis D.

The clamp 502 can include a first plate 504 and a second plate 506. The first and second plates 504 and 506 can be offset from one another along the first direction. The first and second plates 504 and 506 can have inner surfaces 508 that face one another. In one embodiment, the inner surfaces 508 and can define at least one notch 510 that extends into at least one of the inner surfaces 508 and is configured to receive the first end 106 of the reference array body 102. For example, the inner surfaces 508 can define opposing notches 510. The at least one notch can have a non-circular cross-section that is configured to engage a non-circular cross-section of the first end 106 of the reference array body 102 so as to prevent the reference array body 102 from rotating when the clamp 500 is in the clamped position. For example, the at least one notch can define a cross-sectional shape that is a hexagon, an octagon, or any other polygon or suitable shape.

The clamp 502 can include a hinge 512 that couples the first and second plates 504 and 506 to one another such that they are rotatable relative to one another. The hinge 512 can be define a pivot axis F that extends along the first direction that is parallel to the axis D. Thus, the first and second plates 504 and 506 can be configured to pivot about the pivot axis F towards one another to the clamped position and away from one another to the unclamped position.

The adapter 500 can include an actuator 501 configured to selectively control rotation of the reference array body 102 relative to the attachment assembly (e.g., 400, 600, 700) about an axis E that extends along a direction that is perpendicular to the axis D of the patient reference array 100. The actuator 501 can be configured to transition between an unlocked configuration and locked configuration. In the unlocked configuration, the reference array 100 is permitted to rotate relative to the attachment assembly (e.g., 400, 600, 700) about the axis E. In the locked configuration, the reference array 100 is rotationally fixed relative to the attachment assembly (e.g., 400, 600, 700) with respect to rotation about the axis E.

To support the locked and unlocked configuration, the actuator 501, and hence the adapter 500, can include a fastener 520 that is configured to attach the clamp 502 to the attachment assembly (e.g., 400, 600, 700). The fastener 520 can include a shaft 522 having a first end 524 and a second end 526. The first end 524 can be configured to attach to the attachment assembly (e.g., 400, 600, 700). For example, the first end 524 can include threading that is configured to engage threading of the attachment assembly (e.g., 400, 600, 700). The second end 526 can include a drive surface 528 that is configured to be engaged by a user or instrument to turn the fastener 520. In one example, the drive surface 528 can define a handle. The drive surface 528 can be enlarged to have a cross-sectional dimension that is greater than a cross-sectional dimension of the shaft 522.

The first and second plates 504 and 506 can each define an aperture 514 therethrough that is configured to receive the shaft 522 of the fastener 520. The apertures 514 can be aligned with one another so as to receive the shaft 522 therethrough. The fastener 520 extends through the clamp 502 such that the first end 524 extends out of the first plate 504 is a direction that extends from the second plate 506 to the first plate 504, and the second end 526 extends out of the second plate 506, opposite the first end 524, along a direction that extends from the first plate 504 to the second plate 506.

The adapter 500 can include a biasing element 540, such as a spring, that is disposed between the second end 526 of the fastener 520 (e.g., the handle), and the second plate 506. The biasing element 540 can be configured to bias the fastener 520 along a direction that extends from the first plate 504 towards the second plate 506. Thus, the biasing element 540 can be configured to urge the attachment assembly (e.g., 400, 600, 700) against the outer surface of the first plate 504 when the fastener 520 is attached to the attachment assembly (e.g., 400, 600, 700).

Figure 14:
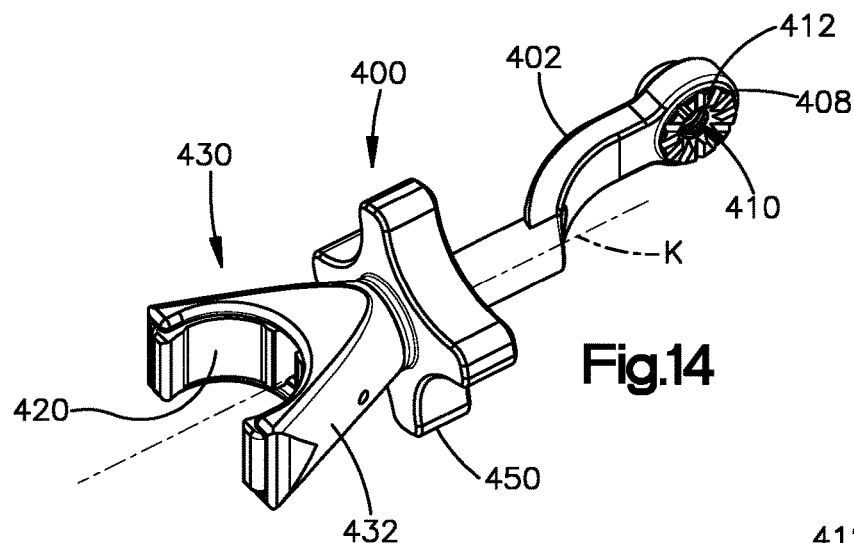
FIG. 14 shows a perspective view of the attachment assembly of FIG. 1 according to one embodiment.
Figure 15:
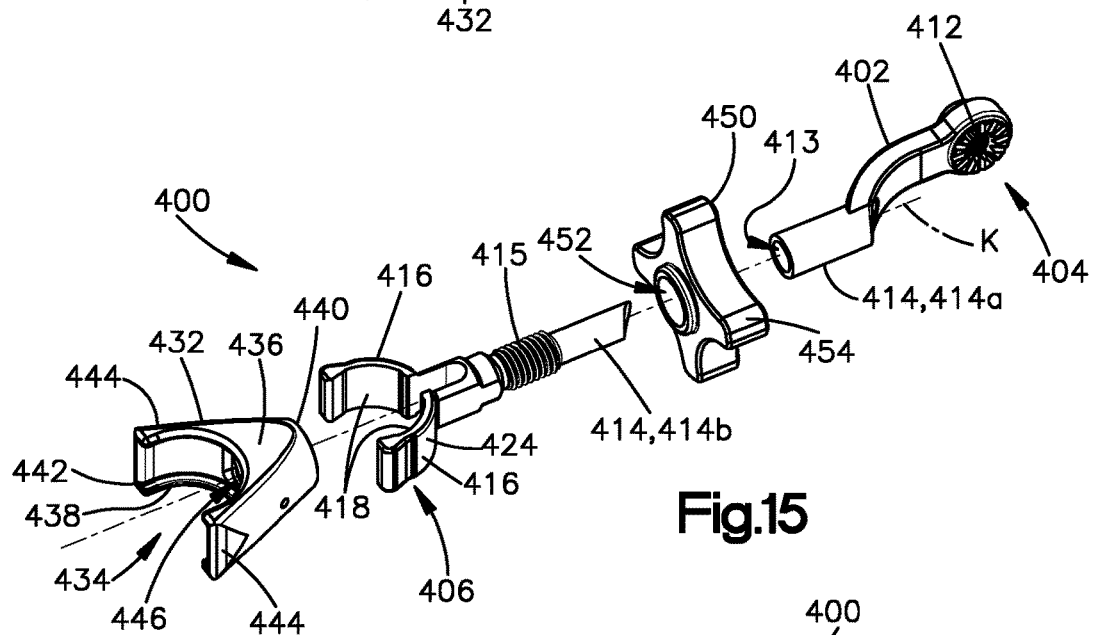
FIG. 15 shows an exploded perspective view of the attachment assembly of FIG. 1 according to one embodiment.
Figure 16:
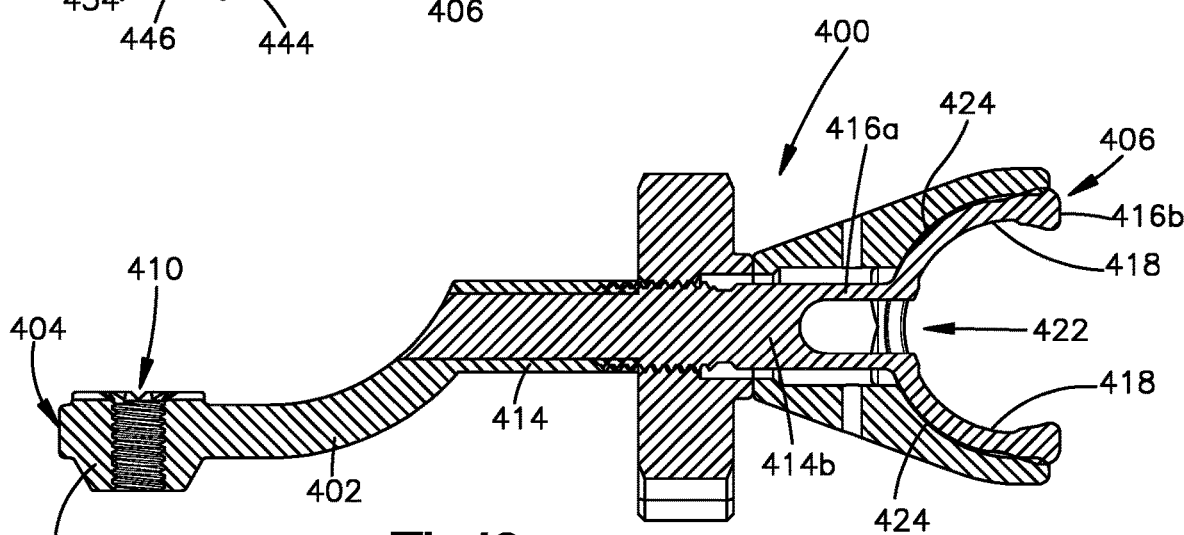
FIG. 16 shows a cross-sectional view of the attachment assembly of FIG. 1 according to one embodiment.

The force exerted by the biasing element 540 between the first plate 504 and the attachment assembly (e.g., 400, 600, 700) can be sufficient to limit or prevent rotation of the reference array body 102 relative to the attachment assembly (e.g., 400, 600, 700), and hence relative to the bone fixation element 200. In some embodiments, the adapter 500 and the attachment assembly (e.g., 400, 600, 700) can include mating geometries that mate with one another when the biasing element 540 biases the attachment assembly (e.g., 400, 600, 700) against the adapter 500 so as to prevent rotation of the body 102 of the patient reference array 100 relative to the attachment assembly (e.g., 400, 600, 700). For example, the first plate 504 can include a surface geometry 511 on an outer surface 509 of the first plate 504 that is configured to engage a corresponding surface geometry (see, for example, geometry 412 in FIGS. 12, 14, and 18) of the attachment assembly (e.g., 400, 600, 700). The surface geometry 511 can include a plurality of protrusions, such as teeth, that are spaced apart from one another by recesses. The protrusions and recesses of the surface geometry 511 can be configured to mate with corresponding protrusions and recesses of the attachment assembly (e.g., 400, 600, 700) so as to fix a rotational position of the reference array 100. The protrusions and recesses can extend radially from the aperture 514 of the first plate 504. The protrusions and recesses can be offset from one another circumferentially around the aperture 514. It will be understood that the mating geometries can be configured in another manner.

In operation, an external force can be applied to the fastener 520 along an actuation direction that extends from the second plate 506 towards the first plate 504 so as to compress the biasing element 540. This in turn causes the first end 524 of the fastener 520, and hence the attachment assembly (e.g., 400, 600, 700) attached to the first end 524, to move along the actuation direction such that the surface geometry of the attachment assembly (e.g., 400, 600, 700) disengages from the surface geometry 511 of the adapter 500. While the external force is applied, the body 102 of the patient reference array 100 can be rotated relative to the attachment assembly (e.g., 400, 600, 700) to a desired position. The external force can then be released so that the biasing element 540 urges the attachment assembly (e.g., 400, 600, 700) against the adapter 500 so as to interlock the mating geometries of the attachment assembly (e.g., 400, 600, 700) and the adapter 500, thereby fixing a position of the reference array body 102 relative to the attachment assembly (e.g., 400, 600, 700).

Turning now to the embodiment of FIGS. 11 to 13, a system 10 is shown having an attachment assembly 600 that couples a patient reference array 100 to a medical implant 200. The reference array 100, the medical implant 200, the fixation post 300, and the adapter 500 can each be implemented as described above. The attachment assembly 600 includes an arm 402 configured to support the patient reference array 100, and a coupler 628 supported by the arm 402. The arm 402 can have a first end 404 and a second end 406 that are offset from one another. The arm 402 can define a shaft 414 that extends between the first and second ends 404 and 406. The first end 404 can have a coupler 408 that is configured to couple to the patient reference array 100. In one example, the coupler 408 can define an opening 410 that is configured to receive the fastener 520 of the adapter 500 (see FIGS. 9 and 10). For example, the opening 410 can include internal threading that engages the threading of the first end 524 of the fastener 520 of the adapter 500. However, it will be understood that the first end 404 can be otherwise configured to couple to the patient reference array 100. In alternative embodiments, the arm 402 can be fixedly attached to the reference array body 102, such as monolithic with, adhered to, welded to, or otherwise fixedly attached to the reference array body 102.

The coupler 408 can include a surface geometry 412 on an outer surface of the arm 402 that is configured to engage a corresponding surface geometry 511 of the adapter 500. The surface geometry 412 can include a plurality of protrusions, such as teeth, that are spaced apart from one another by recesses. The protrusions and recesses can extend radially from the opening 410. The protrusions and recess can be circumferentially offset from one another about the opening 410. However, it will be understood that the surface geometry 511 can be configured in another manner. The protrusions and recesses of the surface geometry 412 can be configured to mate with corresponding protrusions and recesses of the adapter 500 so as to fix a rotational position of the reference array 100 relative to the attachment assembly 600, and hence relative to the pedicle screw 200.

The coupler 628 can comprise a fixation body 630 and an actuator 650. The fixation body 630 can be attached to the arm 402 at the second end 406. For example, the fixation body 630 can be fixedly attached to the arm 402 as shown or can be removably attached to the arm 402. The fixation body 630 has a first end 632 and a second end 634 that are spaced from one another along a central axis H. The fixation body 630 can have an outer surface 636 that extends between the first end 632 and the second end 634. The outer surface 636 can be curved such that the fixation body 630 has a cylindrical shape, although it will be understood that the fixation body 630 can have any other suitable shape such as (without limitation) a cube. The arm 402 can extend from the outer surface 636. In some examples, the arm 402 can have an axis that intersects the central axis of the H.

The fixation body 630 has an inner surface 638, opposite the outer surface 636. The inner surface 638 defines a fixation body recess 640 that extends into the first end 632 towards the second end 634. The recess 634 can terminate before the second end 634, such as at an inner surface of the second end 634. The recess 640 is configured to receive an end of a shaft of a medical implant, such as the proximal end 304 of the fixation shaft 302 of the fixation post 300, along a direction that extends along the central axis H. In at least some embodiments, the inner surface 638 can have a non-circular cross-section. The non-circular cross-section can be configured to engage a non-circular cross-section of outer surface 310 of the proximal end 304 of the post 300 so as to prevent relative rotation between the post 300 and the attachment assembly 600. In some examples, the fixation body 630 can extend along a perimeter of the recess 640 on four sides of the recess 640. In some such examples, the fixation body 630 can be solid around an entire perimeter of the recess 640 (e.g., circumferentially solid) such that the fixation body 630 has a cross-section that defines a closed shaped. Thus, the fixation body 630 can be configured such that the shaft of the medical implant (e.g., the post 300) can only be received into the recess 634 along a direction that extends along the central axis H.

The attachment assembly 600 can include an actuator 650 that is configured to secure the fixation body 630 to the medical implant. The actuator 650 can include a shaft 652 having a first end 654 and a second end 656. The second end 634 of the fixation body 630 can define an opening 642 that extends therethrough that is configured to receive the shaft 652. The first end 654 of the shaft 652 can be configured to attach to the post 300. For example, the first end 654 can be configured to be received in the opening 308 in the proximal end 304 of the post 300 so as to secure the attachment assembly 600 to the post 300. The first end 654 can include threading that is configured to engage the threading of the opening 308 of the post 300. The second end 656 can include a drive surface 658 that is configured to be engaged by a user or instrument to turn the actuator 650. In one example, the drive surface 658 can define a handle. The drive surface 658 can be enlarged to have a cross-sectional dimension that is greater than a cross-sectional dimension of the shaft 652. The cross-sectional dimension of the drive surface 658 can be greater than a cross-sectional dimension of the opening 642 such that the drive surface 658 cannot pass through the opening 642.

When the fixation post 300 is received in the fixation body recess 640 and the actuator 650 is received in the opening 308 of the proximal end 304 of the fixation post 300, the proximal end 304 of the fixation post 300 can interfere with the fixation body 630 so as to limit movement of the fixation body 630 relative to the fixation post 300 along a direction that extends from the second end 634 of the fixation body 630 to the first end 632. Further, the actuator 650, such as the enlarged drive surface 658 of the actuator 650 can interfere with fixation body 630 so as to limit movement of the fixation body 630 along a direction that extends from the first end 632 of the fixation body 630 to the second end 634. In this way, the enlarged drive surface 658 and the proximal end 304 of the fixation post 300 can trap the second end 634 of the fixation body 630 therebetween so as to limit movement of the fixation body 630 relative to the post 300 along the axis H.

Turning now to the embodiment of FIGS. 1 and 14 to 16, a system 10 is shown having an attachment assembly 400 that couples a patient reference array 100 to a medical implant 200. The reference array 100, the medical implant 200, the fixation post 300, and the adapter 500 can each be implemented as described above. In general, the attachment assembly 400 includes an arm 402 that is configured to support the patient reference array 100. At least a portion of the arm 402 extends along a central axis K. The attachment assembly 400 includes a coupler 430 supported by the arm 402. The coupler 430 has a fixation body 432 and an actuator 450. The fixation body 432 is movably coupled to the arm 402 such that the fixation body 432 is configured to translate along at least a portion of the arm 402 along the central axis K. The fixation body 432 defines a fixation body recess 434 that is configured to receive at least a portion of the medical implant. The actuator 450 is coupled to the fixation body 432 such that actuation of the actuator 450 causes the fixation body 432 to translate along the arm 402 along the central axis K so as to secure the coupler 430 to a medical implant. The medical implant can be at least one of (i) the bone fixation element 200 and (ii) the fixation post 300 that couples to the bone fixation element 200. For example, the coupler 430 can be configured to couple the attachment assembly 400 to the extension tabs 228 of the bone fixation element 200 by engaging the extension tabs 228. As another example, the coupler 430 can be configured to couple the attachment assembly 400 to the proximal end 304 of the fixation post 300. It will be understood that the attachment assembly 400 can alternatively couple to medical implants other than the bone fixation element 200 and the fixation post 300.

The arm 402 can have a first end 404 and a second end 406 that are offset from one another. The first end 404 can be configured as described above in relation to FIGS. 11 to 13. For example, the first end 404 can include a coupler 408. The coupler 408 can be spaced opposite from the coupler 430. The arm 402 can define a shaft 414 that extends between the first end 404 and the second end 406. In some embodiments, the shaft 414 can include a first portion 414a and a separate second portion 414b (as shown) that are attached to one another. The first portion 414a can include the first end 404, and the second portion 414b can include the second end 406. In other embodiments, the shaft 414 can be a single piece that is monolithic from the first end 404 to the second end 406.

The second end 406 can include at least one engagement member 416 having an engagement surface 418 that is configured to engage the medical implant so as to secure the attachment assembly 400 to the medical implant. The coupler 430 can include the at least one engagement member 416. The at least one engagement member 416, and hence the engagement surface 418, can be fixedly attached to the shaft 414 with respect to movement along the central axis K. When the medical implant is received in the fixation body recess 434 of the fixation body 432, movement of the fixation body 432 along the shaft 414 along the central axis K can cause the at least one engagement surface 418 to apply a locking force to the medical implant, thereby locking a position of the medical device within the fixation body recess 434.

For example, the at least one engagement member 416 can be configured to move between a biased position and a relaxed position. The at least one engagement member 416 can be configured to apply the locking force to the medical device when in the biased position and release the locking force when in the relaxed position. The at least one engagement member 416 can be resiliently biased towards the relaxed position. Thus, movement of the fixation body 432 along the shaft 414 along a first direction can cause the fixation body 432 to apply a biasing force to the at least one engagement member 416 so as to move the at least one engagement member 416 inwardly into the fixation body recess 434 from the relaxed position to the biased position such that the at least one engagement member 416 applies the locking force to the medical implant. Further, movement of the fixation body 432 along the shaft 414 along a second direction, opposite the first direction, can cause the fixation body 432 to remove the biasing force, thereby allowing the engagement member 416 to automatically and resiliently flex outwardly to the relaxed position so as to release the locking force from the medical implant.

In one example, as shown, the at least one engagement member 416 can include first and second engagement members 416. The first and second engagement members 416 can have first and second inner engagement surfaces 418, respectively. Each engagement member 416 can have an outer surface 424, opposite its inner engagement surface 418. The first and second engagement members can define first and second prongs of a yoke 420, respectively. Movement of the fixation body 432 along the arm causes the first and second engagement members 416 to flex towards one another so as to apply a locking force to the medical implant. Thus, the shaft 414 can define a Y-shape with the top of the Y-shape being defined by the first and second engagement members 416. The first and second inner engagement surfaces 418 can be offset from one another so as to define a recess 422 therebetween. At least a portion of the recess 422 can be disposed with the fixation body recess 434.

The first and second engagement surfaces 418 can be offset from one another along a transverse direction (such as a radial direction) that is transverse to the central axis K. At least one, such as both, of the first and second engagement surfaces 418 is movable relative to the other one of the first and second engagement surfaces 418 between the relaxed position and the biased position. At least a portion of the first engagement surface 418 is spaced closer to at least a portion of the second engagement surface 418 in the biased position than in the relaxed position. Thus, the first and second engagement surfaces 418 can be moved towards one another such that they apply a locking force to opposed sides of the medical implant, thereby locking a position of the medical implant relative to the attachment assembly 400.

Each engagement member 416 can define a first end 416a that is attached to a shaft body 414 of the shaft 414, and a second end 416b that is free from attachment to the shaft body 414. The first end 416a can define a hinge about which the engagement member 416 is configured to resiliently flex. Each engagement member 416 can extend away from the central axis K respect to both the axial direction and the transverse direction. Thus, the second end 416b of each engagement member 416 can be outwardly offset from the first end 416a of the engagement member 416 with respect to both the axial and transverse directions. In one example, each engagement member 416 can be curved or angled inwardly as it extends from its second end 416b towards its first end 416a. Thus, at least a portion of each inner engagement surface 418 can be concave. At least a portion of each outer surface 424 can be convex. The first and second engagement members 416 can extend away from one another with respect to the transverse direction.

The fixation body 432 can include an upper end 436 and a lower end 438 that are offset from one another. The fixation body 432 can include a proximal end 440 and a distal end 442 that are offset from one another. The fixation body recess 434 can extend from the upper end 436 to the lower end 438 such that the fixation body recess 434 is open at the upper and lower ends 436 and 438. The fixation body recess 434 can extend from the distal end 442 towards the proximal end 440. The fixation body recess 434 can terminate before the proximal end 440 such that the fixation body recess 434 is open at the distal end 442 but not at the proximal end 440. The fixation body 432 can include first and second prongs 444 that are offset from one another along the transverse direction. The first and second prongs 444 can define the fixation body recess 434 therebetween.

The fixation body 432 can define an aperture 446 that extends from the proximal end 440 to the fixation body recess 434. The shaft 414 can be received through the aperture 444 such that at least a portion of the at least one engagement member 416 is received in the recess 434 and a portion of the shaft 414 extends out of the proximal end 440 of the fixation body 432. For example, the second portion 414b of the shaft 414 can be received through the aperture 444 and into an axial bore 413 in the first portion 414a of the shaft 414. The fixation body 432 can be movable along the shaft 414 along a first direction such that the fixation body 432 applies a biasing force to each of the at least one engagement member 416. For example, the fixation body 432 can be movable such that the first and second prongs 444 apply a biasing force to the outer surface 424 of at least one of the first and second engagement members 416 so as to move at least one of the first and second engagement members 416 towards the other one of the first and second engagement members 416.

The actuator 450 can be positionally fixed to the fixation body 432 with respect to translation along the central axis K. In one example, the actuator 450 can be rotatable relative to the fixation body 432 about the central axis K. For example, the actuator 450 can define a knob. The actuator 450 can have an opening 452 therethrough that is configured to receive at least a portion of the shaft 414 therethrough. The opening 452 can be threaded. Thus, the actuator 450 can be threadedly coupled to threading 415 on the arm 402 such that rotation of the actuator 450 causes actuator 450 to translate along the arm 402 along the central axis K, thereby urging the fixation body 430 to translate along the central axis K. The actuator 450 can include a drive surface 454 that is configured to be engaged by a user or instrument to turn the actuator 450. It will be understood that, in alternative embodiments, the actuator 450 can have other suitable configurations other than a knob.

Turning now to the embodiment of FIGS. 17 to 20, a system 10 has an attachment assembly 700 that couples a patient reference array 100 to a medical implant 200. The reference array 100, the medical implant 200, the fixation post 300, and the adapter 500 can each be implemented as described above. In general, the attachment assembly 700 includes an arm 402 that is configured to support the patient reference array 100. At least a portion of the arm 402 extends along a central axis K. The attachment assembly 700 includes a coupler 730 supported by the arm 402. The coupler 730 has a fixation body 732 and an actuator 750. The fixation body 732 is movably coupled to the arm 402 such that the fixation body 732 is configured to translate along at least a portion of the arm 402 along the central axis K. The fixation body 732 defines a fixation body recess 734 that is configured to receive at least a portion of the medical implant. The actuator 750 is coupled to the fixation body 732 such that actuation of the actuator 750 causes the fixation body 732 to translate along the arm 402 along the central axis K so as to secure the coupler 730 to a medical implant. The medical implant can be at least one of (i) the bone fixation element 200 and (ii) the fixation post 300 that couples to the bone fixation element 200. For example, the coupler 730 can be configured to couple the attachment assembly 700 to the extension tabs 228 of the bone fixation element 200 by engaging the extension tabs 228. As another example, the coupler 730 can be configured to couple the attachment assembly 700 to the proximal end 304 of the fixation post 300. It will be understood that the attachment assembly 700 can alternatively couple to medical implants other than the bone fixation element 200 and the fixation post 300.

The arm 402 can have a first end 404 and a second end 406 that are offset from one another. The first end 404 can be configured as described above in relation to FIGS. 11 to 13. For example, the first end 404 can include a coupler 408. The coupler 408 can be spaced opposite from the coupler 730. The arm 402 can define a shaft 414 that extends between the first end 404 and the second end 406. In some embodiments, the shaft 414 can include a first portion 414*a* and a separate second portion 414*b* (as shown) that are attached to one another. The first portion 414*a* can include the first end 404, and the second portion 414*b* can include the second end 406. In other embodiments, the shaft 414 can be a single piece that is monolithic from the first end 404 to the second end 406.

The second end 406 can include at least one engagement member 716 having an engagement surface 718 that is configured to engage the medical implant so as to secure the attachment assembly 700 to the medical implant. The engagement surface 718 can be an inner engagement surface that faces into the fixation body recess 734. In some examples, the engagement surface 718 can define a recess 720 therein that is configured to cradle (or at least partially conform to) the medical implant. The coupler 730 can include the at least one engagement member 716. When the medical implant is received in the fixation body recess 734 of the fixation body 732, movement of the fixation body 732 along the shaft 414 along the central axis K can cause the at least one engagement surface 718 to apply a locking force to the medical implant, thereby locking a position of the medical device within the fixation body recess 734 as will be further described below.

The at least one engagement member 716 can be movably coupled to the shaft 414 such that the at least one engagement member 716 can translate relative to the shaft 414 along the axis K. For example, the at least one engagement member 416 can be configured to move between a biased position and a relaxed position. The at least one engagement member 416 can be resiliently biased towards the relaxed position. The coupler 730 can include a biasing element 715, such as a spring, that biases the at least one engagement member 716 inwardly into the fixation body recess 734. The at least one engagement member 716 can be configured to move outwardly (e.g., towards the first end 404) when a biasing force is applied to the engagement surface 718. The at least one engagement member 716 can be configured to resiliently move inwardly (i.e., towards the recess 734) when the biasing force is removed. In alternative embodiments, the at least one engagement member 716, and hence the engagement surface 718, can be fixedly attached to the shaft 414 with respect to movement along the central axis K.

The fixation body 732 can include an upper end 736 and a lower end 738 that are offset from one another, such as spaced opposite one another. The fixation body 732 can include a proximal end 740 and a distal end 742 that are offset from one another, such as spaced opposite one another. The fixation body 732 can include a first side 744 and a second side 746 that are offset from one another, such as spaced opposite one another. The first and second sides 744 and 746 can extend between the upper and lower ends 736 and 738 and between the proximal and distal ends 740 and 742. The fixation body recess 734 can extend from the upper end 736 to the lower end 738 such that the fixation body recess 734 is open at the upper and lower ends 736 and 738. The fixation body recess 734 can extend from the first side 744 towards the second side 746. The fixation body recess 734 can terminate before the second side 746 such that the fixation body recess 734 is open at the first side 744 but not at the second side 746. The fixation body 732 can define a second engagement surface 748 that faces into the fixation body recess 734, such as towards the engagement surface 718. The fixation body recess 734 can be defined between the second engagement surface 748 and the engagement surface 718. As shown, the fixation body 732 can define a U-shape or C-shape about the fixation body recess 734.

The fixation body 732 can define an aperture 745 that extends from the proximal end 740 to the fixation body recess 734. The shaft 414 can be received through the aperture 745 such that at least a portion of the at least one engagement member 716 is received in the recess 734 and a portion of the shaft 414 extends out of the proximal end 740 of the fixation body 732. For example, the second portion 414*b* of the shaft 414 can be received through the aperture 745 and into an axial bore 413 in the first portion 414*a* of the shaft 414.

The fixation body 732 can be movable along the shaft 414 along a first direction (e.g., towards the first end 404) so as to move the engagement surface 748 of the fixation body 732 towards the engagement surface 718 of the engagement member 716. Thus, a distance between the engagement surface 718 and the engagement surface 748 can be decreased. In so doing, the engagement surface 718 of the engagement member and the engagement surface 748 of the fixation body 732 can apply opposing forces to opposing sides of the medical implant so as to lock a position of the medical implant relative to the fixation body 732. The fixation body 732 can be movable along the shaft 414 along a second direction (e.g., away from the first end 404), opposite the first direction, so as to increase a distance between the engagement surface 718 of the engagement member and the engagement surface 748 of the fixation body 732. In so doing, the opposing forces applied to the opposing sides of the medical implant can be released.

The actuation 750 can be positionally fixed to the fixation body 732 with respect to translation along the central axis K. In one example, the actuator 750 can be rotatable relative to the fixation body 732 about the central axis K. For example, the actuator 750 can define a knob. The actuator 750 can have an opening 752 therethrough that is configured to receive at least a portion of the shaft 414 therethrough. The opening 752 can be threaded. Thus, the actuator 750 can be threadedly coupled to threading 415 on the arm 402 such that rotation of the actuator 750 causes actuator 750 to translate along the arm 402 along the central axis K, thereby urging the fixation body 730 to translate along the central axis K. The actuator 750 can include a drive surface 754 that is configured to be engaged by a user or instrument to turn the actuator 750. It will be understood that, in alternative embodiments, the actuator 750 can have other suitable configurations other than a knob.

The actuator 750 can have an actuator body 756 and a connector 756 that is attached to the actuator body 756. The actuator body can define the drive surface 754. The connector 756 is configured to secure the actuator 750 to the fixation body 732 such that the actuator 750 is fixed to the fixation body 732 with respect to translation along the central axis K and rotatable relative to the fixation body 732. The connector 756 can have a generally cylindrical shape with a circumferential groove 758 extending around a circumference of the connector 756. For example, the connector 756 can have a shape similar to a spool. The connector 756 can have a central axis that is aligned with the central axis K. The opening 752 can extend through the connector 756 such that the connector 756 is configured to receive at least a portion of the shaft 414 therethrough.

To secure the actuator 750 to the fixation body 732, the fixation body 732 can define at least one, such as two, securement apertures 735 that extend into at least one of the upper and lower surfaces 736 and 738 and towards the other one of the upper and lower surfaces 736 and 738. Further, the coupler 730 can include at least one, such as two, rods 737 that are configured to be received into the securement apertures 735 and into engagement with the circumferential groove 758 of the actuator 750. For example, a pair of the rods 737 can be engaged with the circumferential groove 758 or opposed sides of the connector 756. The connector 756, and hence the actuator body 756, are permitted to rotate about the axis K as the at least one rod 737 rides along the circumferential groove 758.

Although there has been shown and described the certain embodiments of the present disclosure, it will be readily apparent to those skilled in the art that modifications may be made thereto which do not exceed the scope of the appended claims. The embodiments described in connection with the illustrated embodiments have been presented by way of illustration, and the present invention is therefore not intended to be limited to the disclosed embodiments. Furthermore, the structure and features of each the embodiments described above can be applied to the other embodiments described herein. Accordingly, those skilled in the art will realize that the invention is intended to encompass all modifications and alternative arrangements included within the spirit and scope of the invention, as set forth by the appended claims.

It should be noted that the illustrations and descriptions of the examples and embodiments shown in the figures are for exemplary purposes only, and should not be construed limiting the disclosure. One skilled in the art will appreciate that the present disclosure contemplates various embodiments. Additionally, it should be understood that the concepts described above with the above-described examples and embodiments may be employed alone or in combination with any of the other examples and embodiments described above. It should further be appreciated that the various alternative examples and embodiments described above with respect to one illustrated embodiment can apply to all examples and embodiments as described herein, unless otherwise indicated.

Unless explicitly stated otherwise, each numerical value and range should be interpreted as being approximate as if the word "about," "approximately," or "substantially" preceded the value or range. The terms "about," "approximately," and "substantially" can be understood as describing a range that is within 15 percent of a specified value unless otherwise stated.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While certain example embodiments have been described, these embodiments have been presented by way of example only and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

What is claimed is:

1. A system configured to attach a patient reference array of a computer-assisted
surgery system to a patient, the system comprising: a fixation post having a shaft that has a proximal end and a distal end that are offset from one another along a central axis, the fixation post having a threaded fastener adjacent the distal end that is coupled to the shaft, the threaded fastener configured rotate relative to the shaft about the central axis so as to engage threads of an anchor seat of a pedicle screw, thereby causing the distal end of the shaft to translate into the anchor seat along the central axis and urge the pedicle screw to transition from an unlocked configuration, wherein a screw of the pedicle screw is configured to pivot relative to the anchor seat of the pedicle screw, to a locked configuration, wherein a position of the screw is fixed relative to the anchor seat of the pedicle screw; and an attachment assembly comprising:

an arm configured to support the patient reference array; and a coupler supported by the arm, the coupler comprising: a fixation body defining a recess that is configured to receive at least a portion of the fixation post; and an actuator that is configured to secure the attachment assembly to the fixation post when the at least a portion of the fixation post is received in the recess, wherein: at least a portion of the arm extends along a central axis; the fixation body is movably coupled to the arm such that the fixation body is configured to translate along at least a portion of the arm along the central axis of the arm.

2. The system of claim 1, wherein the shaft is sized such that, when the distal end of the shaft is received in the anchor seat, the shaft is received between extension tabs of the anchor seat and the proximal end of the shaft extends beyond the extension tabs.

3. The system of claim 1, wherein the distal end of the shaft includes an opening that extends through an outer surface of the shaft along a transverse direction that is transverse to the central axis, and the threaded fastener is disposed in the opening.

4. The system of claim 1, wherein the shaft has an outer surface at the proximal end that has a non-circular cross-section configured to engage a non-circular cross-section of the attachment assembly so as to prevent relative rotation between the shaft and the attachment assembly.

5. The system of claim 1, wherein:
the proximal end of the shaft defines a bore hole that extend towards the distal end of the shaft; and
the fixation body has a first end and a second end that are spaced from one another along a central axis, and the recess of the fixation body extends into the first end and terminates before the second end such that the recess is configured to receive the proximal end of the shaft along the central axis of the fixation body; and
the actuator has a shaft that extends into the recess and that is configured to be received in the bore hole of the fixation shaft so as to secure the fixation body to the fixation shaft.

6. The system of claim 1, wherein: the actuator that is coupled to the fixation body such that actuation of the actuator causes the fixation body to translate along the arm along the central axis of the arm so as to secure the fixation body to the fixation post.

7. The system of claim 6, wherein the system comprises first and second engagement members that define first and second prongs of a yoke, respectively, and movement of the fixation body along the arm causes the first and second engagement members to flex towards one another so as to apply a locking force to the medical implant when at least a portion of the medical implant is received between the first and second engagement members.

8. The system of claim 6, wherein:
the arm includes a first engagement surface and the fixation body includes a second engagement surface, the first and second engagement surfaces facing one another so as to define the recess therebetween; and
movement of the fixation body along a first direction causes the second engagement surface to move towards the engagement surface such that, when at least a portion of the medical implant is disposed between the engagement surface and the second engagement surface, the engagement surface and the second engagement surface apply opposing forces to opposing sides of the medical implant so as to lock a position of the medical implant relative to the fixation body.

\* \* \* \* \*